United States Patent
Weng et al.

(10) Patent No.: US 8,137,274 B2
(45) Date of Patent: Mar. 20, 2012

(54) METHODS TO DELIVER HIGH INTENSITY FOCUSED ULTRASOUND TO TARGET REGIONS PROXIMATE BLOOD VESSELS

(75) Inventors: Lee Weng, Bellevue, WA (US); David M Perozek, Mercer Island, WA (US); Jimin Zhang, Bellevue, WA (US)

(73) Assignee: Kona Medical, Inc., Palo Alto, CA (US)

( * ) Notice: Subject to any disclaimer, the term of this patent is extended or adjusted under 35 U.S.C. 154(b) by 0 days.

(21) Appl. No.: 13/025,959

(22) Filed: Feb. 11, 2011

(65) Prior Publication Data
US 2011/0178403 A1     Jul. 21, 2011

Related U.S. Application Data

(63) Continuation of application No. 12/896,740, filed on Oct. 1, 2010, which is a continuation of application No. 11/619,996, filed on Jan. 4, 2007, now abandoned, which is a continuation of application No. 10/616,831, filed on Jul. 10, 2003, now abandoned, which is a continuation of application No. 09/696,076, filed on Oct. 25, 2000, now Pat. No. 6,656,136.

(60) Provisional application No. 60/171,703, filed on Dec. 23, 1999, provisional application No. 60/163,466, filed on Oct. 25, 1999.

(51) Int. Cl.
*A61B 8/00*     (2006.01)
(52) U.S. Cl. ........ 600/437; 600/407; 600/439; 600/443; 600/444; 600/448; 600/454; 601/2
(58) Field of Classification Search .................. 600/407, 600/437, 439, 443, 444, 448, 454; 601/2
See application file for complete search history.

(56) References Cited

U.S. PATENT DOCUMENTS

| | | | |
|---|---|---|---|
| 385,256 | A | 6/1888 | Eggers |
| 3,499,437 | A | 3/1970 | Balamuth |
| 3,552,382 | A | 1/1971 | Mount |

(Continued)

FOREIGN PATENT DOCUMENTS

DE     4230415     3/1994
(Continued)

OTHER PUBLICATIONS

Accord et al., "The Issue of Transmurality in Surgical Ablation for Atrial Fibrillation." Cardiothoracic Surgery Network: 3pp, Feb. 8, 2007.

(Continued)

*Primary Examiner* — James Kish
(74) *Attorney, Agent, or Firm* — Knobbe, Martens, Olson & Bear LLP

(57) ABSTRACT

Methods for applying heat to a region proximate a blood vessel are disclosed. In one embodiment, a method can include generating an imaging ultrasound beam adapted to image a blood vessel target and receiving a reflection of the imaging ultrasound beam. The method can also include producing an output signal in response to the reflection of the imaging ultrasonic beam and processing the output signal to identify a location of a treatment zone proximate an outer wall of the blood vessel. Therapeutic energy can be applied to the treatment zone. In some embodiments, the therapeutic ultrasound energy beam can be moved to over-scan the treatment zone. Other methods are also disclosed.

30 Claims, 10 Drawing Sheets

U.S. PATENT DOCUMENTS

| | | |
|---|---|---|
| 3,847,016 A | 11/1974 | Ziedonis |
| 3,927,662 A | 12/1975 | Ziedonis |
| 4,059,098 A | 11/1977 | Murdock |
| 4,167,180 A | 9/1979 | Kossoff |
| 4,197,856 A | 4/1980 | Northrop |
| 4,206,763 A | 6/1980 | Pedersen |
| 4,237,901 A | 12/1980 | Taenzer |
| 4,273,127 A | 6/1981 | Auth et al. |
| 4,469,099 A | 9/1984 | McEwen |
| 4,479,494 A | 10/1984 | McEwen |
| 4,484,569 A | 11/1984 | Driller et al. |
| 4,545,386 A | 10/1985 | Hetz et al. |
| 4,601,296 A | 7/1986 | Yerushalmi |
| 4,605,010 A | 8/1986 | McEwen |
| 4,688,578 A | 8/1987 | Takano et al. |
| 4,708,836 A | 11/1987 | Gain et al. |
| 4,748,985 A | 6/1988 | Nagasaki |
| 4,757,820 A | 7/1988 | Itoh |
| 4,770,175 A | 9/1988 | McEwen |
| 4,773,865 A | 9/1988 | Baldwin |
| 4,784,148 A | 11/1988 | Dow et al. |
| 4,841,979 A | 6/1989 | Dow et al. |
| 4,850,363 A | 7/1989 | Yanagawa |
| 4,858,613 A | 8/1989 | Fry et al. |
| 4,905,672 A | 3/1990 | Schwarze et al. |
| 4,913,155 A | 4/1990 | Dow et al. |
| 4,929,246 A | 5/1990 | Sinofsky |
| 4,931,047 A | 6/1990 | Broadwin et al. |
| 4,938,216 A | 7/1990 | Lele |
| 4,938,217 A | 7/1990 | Lele |
| 4,957,099 A | 9/1990 | Hassler |
| 5,005,579 A | 4/1991 | Wurster et al. |
| RE33,590 E | 5/1991 | Dory |
| 5,026,387 A | 6/1991 | Thomas |
| 5,036,855 A | 8/1991 | Fry et al. |
| 5,039,774 A | 8/1991 | Shikinami et al. |
| 5,065,742 A | 11/1991 | Belikan et al. |
| 5,080,101 A | 1/1992 | Dory |
| 5,080,102 A | 1/1992 | Dory |
| 5,150,712 A | 9/1992 | Dory |
| 5,170,790 A | 12/1992 | Lacoste et al. |
| 5,178,135 A | 1/1993 | Uchiyama et al. |
| 5,178,148 A | 1/1993 | Lacoste et al. |
| 5,181,522 A | 1/1993 | McEwen |
| 5,194,291 A | 3/1993 | D'Aoust et al. |
| 5,211,160 A | 5/1993 | Talish et al. |
| 5,215,680 A | 6/1993 | D'Arrigo |
| 5,219,401 A | 6/1993 | Cathignol et al. |
| 5,230,334 A | 7/1993 | Klopotek |
| 5,230,921 A | 7/1993 | Waltonen et al. |
| 5,233,994 A | 8/1993 | Shmulewitz |
| 5,243,988 A | 9/1993 | Sieben et al. |
| 5,254,087 A | 10/1993 | McEwen |
| 5,263,957 A | 11/1993 | Davison |
| 5,290,278 A | 3/1994 | Anderson |
| 5,311,869 A | 5/1994 | Okazaki |
| 5,312,431 A | 5/1994 | McEwen |
| 5,352,195 A | 10/1994 | McEwen |
| 5,364,389 A | 11/1994 | Anderson |
| 5,383,896 A | 1/1995 | Gershony et al. |
| 5,391,140 A | 2/1995 | Schaetzle et al. |
| 5,391,197 A | 2/1995 | Burdette et al. |
| 5,394,877 A | 3/1995 | Orr et al. |
| 5,415,657 A | 5/1995 | Taymor-Luria |
| 5,439,477 A | 8/1995 | McEwen |
| 5,453,576 A | 9/1995 | Krivitski |
| 5,454,373 A | 10/1995 | Koger et al. |
| 5,454,831 A | 10/1995 | McEwen |
| 5,471,988 A | 12/1995 | Fujio et al. |
| 5,474,071 A | 12/1995 | Chapelon et al. |
| 5,492,126 A | 2/1996 | Hennige et al. |
| 5,503,152 A | 4/1996 | Oakley et al. |
| 5,507,744 A | 4/1996 | Tay et al. |
| 5,507,790 A | 4/1996 | Weiss |
| 5,515,853 A | 5/1996 | Smith et al. |
| 5,520,188 A | 5/1996 | Hennige et al. |
| 5,522,878 A | 6/1996 | Montecalvo et al. |
| 5,524,620 A | 6/1996 | Rosenschein |
| 5,526,815 A | 6/1996 | Granz et al. |
| 5,534,232 A | 7/1996 | Denes et al. |
| 5,536,489 A | 7/1996 | Lohrmann et al. |
| 5,556,415 A | 9/1996 | McEwen et al. |
| 5,558,092 A | 9/1996 | Unger et al. |
| 5,573,497 A | 11/1996 | Chapelon |
| 5,578,055 A | 11/1996 | McEwen |
| 5,584,853 A | 12/1996 | McEwen |
| 5,601,526 A | 2/1997 | Chapelon et al. |
| 5,607,447 A | 3/1997 | McEwen et al. |
| 5,609,485 A | 3/1997 | Bergman et al. |
| 5,626,601 A | 5/1997 | Gershony et al. |
| 5,630,837 A | 5/1997 | Crowley |
| 5,638,823 A | 6/1997 | Akay et al. |
| 5,643,179 A | 7/1997 | Fujimoto |
| 5,649,954 A | 7/1997 | McEwen |
| 5,655,538 A | 8/1997 | Lorraine et al. |
| 5,657,760 A | 8/1997 | Ying et al. |
| 5,665,073 A | 9/1997 | Bulow et al. |
| 5,666,954 A | 9/1997 | Chapelon et al. |
| 5,681,339 A | 10/1997 | McEwen et al. |
| 5,685,307 A | 11/1997 | Holland et al. |
| 5,695,493 A | 12/1997 | Nakajima et al. |
| 5,697,897 A | 12/1997 | Buchholtz et al. |
| D389,574 S | 1/1998 | Emerson et al. |
| 5,711,058 A | 1/1998 | Frey et al. |
| 5,716,374 A | 2/1998 | Francese et al. |
| 5,720,286 A | 2/1998 | Chapelon et al. |
| 5,720,287 A | 2/1998 | Chapelon et al. |
| 5,726,066 A | 3/1998 | Choi |
| 5,735,796 A | 4/1998 | Granz et al. |
| 5,738,635 A | 4/1998 | Chapelon et al. |
| 5,741,295 A | 4/1998 | McEwen |
| 5,755,228 A | 5/1998 | Wilson et al. |
| 5,762,066 A * | 6/1998 | Law et al. ..................... 600/439 |
| 5,769,790 A | 6/1998 | Watkins et al. |
| 5,788,636 A | 8/1998 | Curley |
| 5,807,285 A | 9/1998 | Vaitekunas |
| 5,810,007 A | 9/1998 | Holupka et al. |
| 5,810,810 A | 9/1998 | Tay et al. |
| 5,817,021 A | 10/1998 | Reichenberger |
| 5,823,962 A | 10/1998 | Schaetzle et al. |
| 5,824,015 A | 10/1998 | Sawyer |
| 5,824,277 A | 10/1998 | Campos |
| 5,827,204 A | 10/1998 | Grandia et al. |
| 5,827,268 A | 10/1998 | Laufer |
| 5,833,647 A | 11/1998 | Edwards |
| 5,840,028 A | 11/1998 | Chubachi et al. |
| 5,846,517 A | 12/1998 | Unger |
| 5,852,860 A | 12/1998 | Lorraine et al. |
| 5,853,752 A | 12/1998 | Unger et al. |
| 5,855,589 A | 1/1999 | McEwen et al. |
| 5,873,828 A | 2/1999 | Fujio et al. |
| 5,879,314 A | 3/1999 | Peterson et al. |
| 5,882,302 A | 3/1999 | Driscoll, Jr. et al. |
| 5,895,356 A | 4/1999 | Andrus |
| 5,904,659 A | 5/1999 | Duarte |
| 5,906,580 A | 5/1999 | Kline-Schoder et al. |
| 5,911,735 A | 6/1999 | McEwen |
| 5,919,139 A | 7/1999 | Lin |
| 5,921,994 A | 7/1999 | Andreas et al. |
| 5,922,945 A | 7/1999 | Allmaras et al. |
| 5,931,786 A | 8/1999 | Whitmore, III et al. |
| 5,931,853 A | 8/1999 | McEwen |
| 5,935,144 A | 8/1999 | Estabrook |
| 5,935,146 A | 8/1999 | McEwen |
| 5,935,339 A | 8/1999 | Henderson et al. |
| 5,951,476 A | 9/1999 | Beach |
| 5,957,849 A | 9/1999 | Munro |
| 5,964,782 A | 10/1999 | Lafontaine et al. |
| 5,976,092 A | 11/1999 | Chinn |
| 5,979,453 A | 11/1999 | Savage et al. |
| 5,993,389 A | 11/1999 | Driscoll, Jr. et al. |
| 5,997,481 A | 12/1999 | Adams et al. |
| 6,007,499 A * | 12/1999 | Martin et al. ..................... 601/3 |
| 6,014,473 A | 1/2000 | Hossack et al. |
| 6,033,506 A | 3/2000 | Klett |
| 6,036,650 A | 3/2000 | Wu et al. |
| 6,037,032 A | 3/2000 | Klett et al. |

| | | |
|---|---|---|
| 6,039,694 A | 3/2000 | Larson et al. |
| 6,050,943 A * | 4/2000 | Slayton et al. ............... 600/439 |
| 6,067,371 A | 5/2000 | Gouge et al. |
| 6,068,596 A | 5/2000 | Weth et al. |
| 6,071,239 A | 6/2000 | Cribbs et al. |
| 6,071,277 A | 6/2000 | Farley et al. |
| 6,078,831 A | 6/2000 | Belef et al. |
| 6,083,159 A | 7/2000 | Driscoll, Jr. et al. |
| 6,087,761 A | 7/2000 | Lorraine et al. |
| 6,102,860 A | 8/2000 | Mooney |
| 6,106,463 A | 8/2000 | Wilk |
| 6,120,453 A | 9/2000 | Sharp |
| 6,128,522 A | 10/2000 | Acker et al. |
| 6,179,831 B1 | 1/2001 | Bliweis |
| 6,182,341 B1 | 2/2001 | Talbot et al. |
| 6,200,539 B1 | 3/2001 | Sherman et al. |
| 6,206,843 B1 | 3/2001 | Iger et al. |
| 6,213,939 B1 | 4/2001 | McEwen |
| 6,217,530 B1 | 4/2001 | Martin et al. |
| 6,221,015 B1 | 4/2001 | Yock |
| 6,231,507 B1 | 5/2001 | Zikorus et al. |
| 6,233,477 B1 | 5/2001 | Chia et al. |
| 6,246,156 B1 | 6/2001 | Takeuchi et al. |
| 6,254,601 B1 | 7/2001 | Burbank et al. |
| 6,263,551 B1 | 7/2001 | Lorraine et al. |
| 6,267,734 B1 | 7/2001 | Ishibashi et al. |
| 6,270,458 B1 | 8/2001 | Barnea |
| 6,277,077 B1 | 8/2001 | Brisken et al. |
| 6,315,441 B2 | 11/2001 | King |
| 6,332,089 B1 | 12/2001 | Acker et al. |
| 6,361,496 B1 | 3/2002 | Zikorus et al. |
| 6,361,548 B1 | 3/2002 | McEwen |
| 6,399,149 B1 | 6/2002 | Klett et al. |
| 6,406,759 B1 | 6/2002 | Roth |
| 6,409,720 B1 | 6/2002 | Hissong et al. |
| 6,419,669 B1 | 7/2002 | Frazier et al. |
| 6,425,867 B1 | 7/2002 | Vaezy et al. |
| 6,425,876 B1 | 7/2002 | Frangi et al. |
| 6,432,067 B1 | 8/2002 | Martin et al. |
| 6,443,894 B1 | 9/2002 | Sumanaweera et al. |
| 6,453,526 B2 | 9/2002 | Lorraine et al. |
| 6,488,639 B1 | 12/2002 | Ribault et al. |
| 6,491,672 B2 | 12/2002 | Slepian et al. |
| 6,494,848 B1 | 12/2002 | Sommercorn et al. |
| 6,500,133 B2 | 12/2002 | Martin et al. |
| 6,522,926 B1 | 2/2003 | Kieval et al. |
| 6,548,047 B1 | 4/2003 | Unger |
| 6,551,576 B1 | 4/2003 | Unger et al. |
| 6,559,644 B2 | 5/2003 | Froundlich et al. |
| 6,562,037 B2 | 5/2003 | Paton et al. |
| 6,565,557 B1 | 5/2003 | Sporri et al. |
| 6,576,168 B2 | 6/2003 | Hardcastle et al. |
| 6,584,360 B2 | 6/2003 | Francischelli et al. |
| 6,595,934 B1 | 7/2003 | Hissong et al. |
| 6,599,256 B1 | 7/2003 | Acker et al. |
| 6,599,288 B2 | 7/2003 | Maguire et al. |
| 6,602,251 B2 | 8/2003 | Burbank et al. |
| 6,612,988 B2 | 9/2003 | Maor et al. |
| 6,616,624 B1 | 9/2003 | Kieval |
| 6,626,855 B1 | 9/2003 | Weng et al. |
| 6,633,658 B1 | 10/2003 | Dabney et al. |
| 6,652,461 B1 | 11/2003 | Levkovitz |
| 6,656,131 B2 | 12/2003 | Alster et al. |
| 6,656,136 B1 | 12/2003 | Weng et al. |
| 6,676,601 B1 | 1/2004 | Lacoste et al. |
| 6,685,639 B1 | 2/2004 | Wang et al. |
| 6,706,892 B1 | 3/2004 | Ezrin et al. |
| 6,709,392 B1 | 3/2004 | Salgo et al. |
| 6,709,407 B2 | 3/2004 | Fatemi |
| 6,716,184 B2 | 4/2004 | Vaezy et al. |
| 6,719,694 B2 | 4/2004 | Weng et al. |
| 6,719,699 B2 | 4/2004 | Smith |
| 6,726,627 B1 | 4/2004 | Lizzi et al. |
| 6,735,461 B2 | 5/2004 | Vitek et al. |
| 6,755,789 B2 | 6/2004 | Stringer et al. |
| 6,764,488 B1 | 7/2004 | Burbank et al. |
| 6,846,291 B2 | 1/2005 | Smith et al. |
| 6,875,176 B2 | 4/2005 | Mourad et al. |
| 6,875,420 B1 | 4/2005 | Quay |
| 6,905,498 B2 | 6/2005 | Hooven |
| 6,932,771 B2 | 8/2005 | Whitmore et al. |
| 6,955,648 B2 | 10/2005 | Mozayeni et al. |
| 6,978,174 B2 | 12/2005 | Gelfand et al. |
| 7,022,077 B2 | 4/2006 | Mourad et al. |
| 7,052,463 B2 | 5/2006 | Peszynski et al. |
| 7,063,666 B2 | 6/2006 | Weng et al. |
| 7,128,711 B2 | 10/2006 | Medan et al. |
| 7,149,564 B2 | 12/2006 | Vining et al. |
| 7,162,303 B2 | 1/2007 | Levin et al. |
| 7,211,060 B1 | 5/2007 | Talish et al. |
| 7,260,250 B2 | 8/2007 | Summers et al. |
| 7,285,093 B2 | 10/2007 | Anisimov et al. |
| 7,445,599 B2 | 11/2008 | Kelly et al. |
| 7,470,241 B2 | 12/2008 | Weng et al. |
| 7,499,748 B2 | 3/2009 | Moffitt et al. |
| 7,510,536 B2 | 3/2009 | Foley et al. |
| 7,530,958 B2 | 5/2009 | Slayton et al. |
| 7,534,209 B2 | 5/2009 | Abend |
| 7,617,005 B2 | 11/2009 | Demarais et al. |
| 7,620,451 B2 | 11/2009 | Demarais et al. |
| 7,628,764 B2 | 12/2009 | Duarte et al. |
| 7,684,865 B2 | 3/2010 | Aldrich et al. |
| 7,697,972 B2 | 4/2010 | Verard et al. |
| 2001/0014775 A1 | 8/2001 | Koger et al. |
| 2001/0014805 A1 | 8/2001 | Burbank et al. |
| 2001/0032382 A1 | 10/2001 | Lorraine et al. |
| 2001/0041910 A1 | 11/2001 | McEwen |
| 2001/0044636 A1 | 11/2001 | Pedros et al. |
| 2002/0095164 A1 | 7/2002 | Andreas et al. |
| 2002/0193831 A1 | 12/2002 | Smith, III |
| 2003/0009194 A1 | 1/2003 | Saker et al. |
| 2003/0018255 A1 | 1/2003 | Martin et al. |
| 2003/0036771 A1 | 2/2003 | McEwen |
| 2003/0050665 A1 | 3/2003 | Ginn |
| 2003/0069569 A1 | 4/2003 | Burdette et al. |
| 2003/0120204 A1 | 6/2003 | Unger et al. |
| 2003/0153849 A1 | 8/2003 | Huckle et al. |
| 2003/0195420 A1 | 10/2003 | Mendlein et al. |
| 2003/0208101 A1 | 11/2003 | Cecchi |
| 2004/0002654 A1 | 1/2004 | Davidson et al. |
| 2004/0030268 A1 | 2/2004 | Weng et al. |
| 2004/0054287 A1 | 3/2004 | Stephens |
| 2004/0054289 A1 | 3/2004 | Eberle et al. |
| 2004/0078034 A1 | 4/2004 | Acker et al. |
| 2004/0078219 A1 | 4/2004 | Kaylor |
| 2004/0097840 A1 | 5/2004 | Holmer |
| 2004/0106880 A1 | 6/2004 | Weng et al. |
| 2004/0113524 A1 | 6/2004 | Baumgartner et al. |
| 2004/0122493 A1 | 6/2004 | Ishibashi et al. |
| 2004/0127798 A1 | 7/2004 | Dala-Krishna et al. |
| 2004/0153126 A1 | 8/2004 | Okai |
| 2004/0158154 A1 | 8/2004 | Hanafy et al. |
| 2004/0234453 A1 | 11/2004 | Smith |
| 2004/0254620 A1 | 12/2004 | Lacoste et al. |
| 2005/0043625 A1 | 2/2005 | Oliver et al. |
| 2005/0046311 A1 | 3/2005 | Baumgartner et al. |
| 2005/0065436 A1 | 3/2005 | Ho et al. |
| 2005/0070790 A1 | 3/2005 | Niwa et al. |
| 2005/0090104 A1 | 4/2005 | Yang et al. |
| 2005/0096542 A1 | 5/2005 | Weng et al. |
| 2005/0154299 A1 | 7/2005 | Hoctor et al. |
| 2005/0182319 A1 | 8/2005 | Glossop |
| 2005/0240102 A1 | 10/2005 | Rachlin et al. |
| 2005/0240170 A1 | 10/2005 | Zhang et al. |
| 2006/0058678 A1 | 3/2006 | Vitek et al. |
| 2006/0122514 A1 | 6/2006 | Byrd et al. |
| 2006/0184069 A1 | 8/2006 | Vaitekunas |
| 2006/0235300 A1 | 10/2006 | Weng et al. |
| 2007/0179379 A1 | 8/2007 | Weng et al. |
| 2007/0213616 A1 | 9/2007 | Anderson et al. |
| 2007/0233185 A1 | 10/2007 | Anderson et al. |
| 2007/0239000 A1 | 10/2007 | Emery et al. |
| 2008/0033292 A1 | 2/2008 | Shafran |
| 2008/0045864 A1 | 2/2008 | Candy et al. |
| 2008/0045865 A1 | 2/2008 | Kislev |
| 2008/0200815 A1 | 8/2008 | Van Der Steen et al. |
| 2008/0255642 A1 | 10/2008 | Zarins et al. |
| 2008/0319375 A1 | 12/2008 | Hardy |

| | | | |
|---|---|---|---|
| 2009/0012098 A1 | 1/2009 | Jordan et al. |
| 2009/0036948 A1 | 2/2009 | Levin et al. |
| 2009/0054770 A1 | 2/2009 | Daigle |
| 2009/0062697 A1 | 3/2009 | Zhang et al. |
| 2009/0062873 A1 | 3/2009 | Wu et al. |
| 2009/0076409 A1 | 3/2009 | Wu et al. |
| 2009/0088623 A1 | 4/2009 | Vortman et al. |
| 2009/0112095 A1 | 4/2009 | Daigle |
| 2009/0112133 A1 | 4/2009 | Deisseroth et al. |
| 2009/0221939 A1 | 9/2009 | Demarais et al. |
| 2009/0264755 A1 | 10/2009 | Chen et al. |
| 2009/0326379 A1 | 12/2009 | Daigle et al. |
| 2011/0118602 A1 | 5/2011 | Weng et al. |

FOREIGN PATENT DOCUMENTS

| | | |
|---|---|---|
| EP | 0420758 | 4/1991 |
| EP | 1265223 | 12/2002 |
| EP | 1874192 A1 | 10/2006 |
| EP | 2181342 A1 | 2/2009 |
| EP | 2303131 | 12/2009 |
| FR | 2672486 | 8/1992 |
| WO | WO 9731364 | 8/1997 |
| WO | WO 99/48621 | 9/1999 |
| WO | WO 0072919 | 12/2000 |
| WO | WO 01/34018 | 5/2001 |
| WO | WO 02069805 | 9/2002 |
| WO | WO 2005/030295 | 4/2005 |
| WO | WO 2006/113445 | 10/2006 |
| WO | WO 2009/026534 | 2/2009 |
| WO | WO 2009/158399 | 12/2009 |
| WO | WO 2011/053757 | 5/2011 |
| WO | WO 2011/053772 | 5/2011 |

OTHER PUBLICATIONS

Amenta et al., "A New Voronoi-Based Surface Reconstruction Algorithm." Computer Graphics: 7pp, 1998.
American Red Cross., "Blood 101." 4pp., Dec. 11, 2007.
Anand et al., "Monitoring formation of high intensity focused ultrasound (HIFU) induced lesions using backscattered ultrasound." Acoustical Society of America; Mar. 10, 2004.
Anand et al., "Using the ATL 1000 to Collect Domodulated RF Data for Monitoring HIFU Lesion Formation." Presented at SPIE Medical Imaging 2003. 11pp, 2003.
Aurenhammer, F. "Voronoi diagrams—A Survey of a Fundamental Geometric Data Structure." ACM Computing Surveys, vol. 23, No. 3: 345-405, Sep. 1991.
Bachmann et al., "Targeting Mucosal Addressin Cellular Adhesion Molecule (MAdCAM)-1 to Noninvasively Image Experimental Crohn's Disease." Gastroenterology; vol. 130: 8-16, 2006.
Barthe et al. "Efficient Wideband Linear Arrays for Imaging and Therapy" IEEE Ultrasonics Symposium. pp. 1249-1252 (1999).
Bauer et al., "Ultrasound Imaging with SonoVue: Low Mechanical Index Real-Time Imaging." Acad. Radiol.; vol. 9, Suppl. 2: S282-S284, 2002.
Beard et al., "An Annular Focus Ultrasonic Lens for Local Hyperthermia Treatment of Small Tumors." Ultrasound in Medicine & Biology; vol. 8, No. 2: 177-184, 1982.
Bokarewa et al., "Tissue factor as a proinflammatory agent." Arthritis Research, vol. 4: 190-195, Jan. 10, 2002.
Bots et al., "Intima Media Thickness as a Surrogate Marker for Generalised Atherosclerosis." Cardiovascular Drugs and Therapy, ProQuest Medical Library; vol. 16, No. 4: 341-351, Jul. 2002.
Brayman et al., "Erosion of Artificial Endothelia In Vitro by Pulsed Ultrasound: Acoustic Pressure, Frequency, Membrane Orientation and Microbubble Contrast Agent Dependence." Ultrasound in Medicine & Biology; vol. 25, No. 8: 1305-1320, 1999.
Buller et al., "Accurate Three-dimensional Wall Thickness Measurement From Multi-Slice Short-Axis MR Imaging." Computers in Cardiology, 245-248, 1995.
Byram et al., "3-D Phantom and In Vivo Cardiac Speckle Tracking Using a Matrix Array and Raw Echo Data." IEEE Transactions on Ultrasonics, Ferroelectrics, and Frequency Control, vol. 57, No. 4; 839-854, Apr. 2010.
Campese, V., Krol, E. Neurogenic Factors in Renal Hypertension. Current Hypertension Reports 2002, 4:256-260.
Canadian Examination Report dated Nov. 14, 2007 in CA Patent Application 2,387,127, filed Oct. 25, 2000.
Chao et al., "Aspheric lens design." Ultrasonics Symposium, 2000 IEEE, vol. 2: Abstract Only, Oct. 2000.
Chelule et al., "Fabrication of Medical Models From Scan Data via Rapid Prototyping Techniques." 9 pp., Feb. 7, 2007.
Chen et al., "A comparison of the fragmentation thresholds and inertial cavitation doses of different ultrasound contrast agents." Journal of the Acoustical Society of America, vol. 113, No. 1: 643-665, Jan. 2003.
Chen et al., "Inertial Cavitation Dose and Hemolysis Produced In Vitro With or Without Optison." Ultrasound in Medicine & Biology, vol. 29, No. 5: 725-737, 2003.
Chen et al., DC-Biased Electrostrictive Materials and Transducers for Medical Imaging, 1997 IEEE Ultrasonics Symposium, IEEE, Aug. 1997.
Chong et al., "Tissue Factor and Thrombin Mediate Myocardial Ischemia-Reperfusion Injury." The Society of Thoracic Surgeons, vol. 75: S649-655, 2003.
Damianou, et al., "Application of the Thermal Dose Concept for Predicting the Necrosed Tissue Volume During Ultrasound Surgery", IEEE Ultrasonic Symposium, (1993) 1199-1202.
Dayton et al., "The magnitude of radiation force on ultrasound contrast agents." Journal of the Acoustical Society of America, vol. 112, No. 5, Part 1: 2183-2192, Nov. 2002.
Dempsey et al., "Thickness of Carotid Artery Atherosclerotic Plaque and Ischemic Risk." Neurosurgery, vol. 27, No. 3: 343-348, 1990.
Dewhirst, et al., "Basic principles of thermal dosimetry and thermal thresholds for tissue damage from hyperthermia", Int. J. Hyperthermia, (2003) 19(3):267-294.
Dibona, G. F., et al., Chaotic behavior of renal sympathetic nerve activity: effect of baroreceptor denervation and cardiac failure, Am J Physiol Renal Physiol, 279:F491-501, 2000.
Dibona, G.F.: "Neural control of the kidney: functionally specific renal sympathetic nerve fibers." Am J. Physiol Regulatory Integrative Comp Physiol 279: R1517-1524, 2000.
Dibona, GF. Functionally Specific Renal Sympathetic Nerve Fibers: Role in Cardiovascular Regulation. American Journal of Hypertension. 2001 vol. 14(6) 163S-170S.
Doumas, M., et al., Renal Sympathetic Denervation: The Jury is Still Out, The Lancet, Nov. 2010, vol. 376, Issue 9756, pp. 1878-1880.
Ebbini et al., "Image-guided noninvasive surgery with ultrasound phased arrays." SPIE, vol. 3249: 230-239, Apr. 2, 1998.
Edelsbrunner, Herbert. "Geometry and Topology for Mesh Generation." Cambridge University Press: 68pp, 2001.
Esler, Murray D., et al., Renal sympathetic denervation in patients with treatmentresistant hypertension (The Symplicity HTN-2 Trial): a randomised controlled trial, Nov. 2010, The Lancet, vol. 376, Issue 9756, pp. 1903-1909.
European Examination Report dated Mar. 7, 2008 in EP Patent Application 989717.4, filed Oct. 25, 2000.
Everbach et al., "Cavitational Mechanisms in Ultrasound-Accelerated Thrombolysis at 1 MHz." Ultrasound in Medicine & Biology, vol. 26, No. 7: 1153-1160, 2000.
Ewert et al., "Anti-myeloperoxidase antibodies stimulate neutrophils to damage human endothelial cells." Kidney International, vol. 41: 375-383, 1992.
Fjield et al.; "A parametric study of the concentric-ring transducer design for MRI guided ultrasound surgery." J. Acoust. Soc. Am 100 (2) Pt. 1, Aug. 1996.
Ganapathy et al., "A New General Triangulation Method for Planar Contours." Computer Graphics vol. 16, No. 3:69-75, 1982.
Grassi, G. Role of the Sympathetic Nervous System in Human Hypertension. Journal of Hypertension. 1998, 16: 1979-1987.
Gray, Henry. "The Skull." Anatomy of the Human Body: 7pp., 1918.
Guzman et al., "Ultrasound—Mediated Disruption of Cell Membranes. I. Quantification of Molecular uptake and Cell Viability. / II. Heterogeneous effects on cells." Journal of the Acoustical Society of America, vol. 110, No. 1: 588-606, Jul. 2001.

Hachimine, K. et. al. Sonodynamic Therapy of Cancer Using a Novel Porphyrin Derivative, DCPH-P-Na(I),which is Devoid of Photosensitivity. Cancer Science 2007; 98: 916-920.

Hadimioglu et al., "High-Efficiency Fresnel Acoustic Lenses." Ultrasonics Symposium 1993 IEEE: 579-582, 1993.

Han et al., "A Fast Minimal Path Active Contour Model." IEEE Transactions on Image Processing, vol. 10, No. 6: 865-873, Jun. 2001.

Hatangadi, Ram. "A Novel Dual Axis Multiplanar Transesophageal Ultrasound Probe for Three-Dimensional Echocardiograph." University of Washington, Department of Sciences and Engineering, vol. 55-11B: Abstract 1pg, 1994.

Holt et al., "Bubbles and Hifu: the Good, the Bad and the Ugly." Boston University, Department of Aerospace and Mechanical Engineering: 120-131, 2002.

Hubka et al., "Three-dimensional echocardiographic measurement of left ventricular wall thickness: In vitro and in vivo validation." Journal of the American Society of Echocardiography, vol. 15, No. 2: 129-135, 2002.

Hutchinson et al. "Intracavitary Ultrasound Phased Arrays for Noninvasive Prostate Surgery." IEEE Transactions on Ultrasonics. Ferroelectrics, and Frequency Control. 43(6):1032-1042 (1996).

Hwang et al., "Vascular Effects Induced by Combined 1-MHz Ultrasound and Microbubble Contrast Agent Treatments In Vivo." Ultrasound in Medicine & Biology, vol. 31, No. 4: 553-564, 2005.

Hynynen et al., "Potential Adverse Effects of High-Intensity Focused Ultrasound Exposure on Blood Vessels In Vivo." Ultrasound in Medicine & Biology, vol. 22, No. 2: 193-201, 1996.

Iannuzzi et al., "Ultrasonographic Correlates of Carotid Atherosclerosis in Transient Ischemic Attack and Stroke." Stroke, ProQuest Medical Library, vol. 26, No. 4: 614-619, 1995.

Idell et al., "Fibrin Turnover in Lung Inflammation and Neoplasia." American Journal of Respiratory and Critical Care Medicine, vol. 163: 578-584, 2001.

Indman, Paul. "Alternatives in Gynecology." Hysteroscopy, OBGYN.net, Oct. 14, 2004. http://www.gynalternatives.com/hsc.html.

International Preliminary Report on Patentability dated Jun. 5, 2003 for PCT Application No. PCT/US00/35262.

International Search Report and Written Opinion dated Apr. 23, 2001 for PCT Application No. PCT/US00/35262.

International Search Report and Written Opinion dated Aug. 4, 2005 for PCT Application No. PCT/US2005/001893.

International Search Report and Written Opinion dated Jul. 11, 2007 for PCT Application No. PCT/US2006/041163.

International Search Report and Written Opinion dated Jun. 30, 2008 for PCT Application No. PCT/US2007/087310.

International Search Report and Written Opinion dated Mar. 30, 2007 for Application No. PCT/US2006/027688 filed on Jul. 13, 2006.

International Search Report and Written Opinion dated May 18, 2001 for PCT Application No. PCT/US00/41606.

International Search Report and Written Opinion dated May 29, 2007 for PCT Application No. PCT/US04/31506.

Invitation to Pay Additional Fees and Partial International Search Report dated Nov. 29, 2006 for PCT Application No. PCT/US2006/027688.

Janssen, BJ and Smits, J. Renal Nerves in Hypertension. Mineral and Electrolyte Metabolism. 1090; 15:74-82, 1989.

Jolesz, F. MRI-Guided Focused Ultrasound Surgery. Annual Review of Medicine. 2009 60: 417-30.

Kaczkowski et al., "Development of a High Intensity Focused Ultrasound System for Image-Guided Ultrasonic Surgery." Ultrasound for Surgery, Oct. 14, 2004. (http://cimu.apl.washington.edu/hifusurgerysystem.html).

Kang et al., "Analysis of the Measurement Precision of Arterial Lumen and Wall Areas Using High-Resolution MRI." Magnetic Resonance in Medicine, vol. 44: 968-972, 2000.

Klibanov et al., "Detection of Individual Microbubbles of an Ultrasound contrast Agent: Fundamental and Pulse Inversion Imaging." Academy of Radiology, vol. 9, Suppl. 2: S279-S281, 2002.

Kojima, T., Matrix Array Transducer and Flexible Matrix Arry Transducer,Proceedings of the Ultrasonics Symposium, vol. 2:649-653 (1986).

Krum, H et. al. Catheter-Based Renal Sympathetic Denervation for Resistant Hypertension: a Multicentre Safety and Proof-of-Principle Cohort Study. Lancet 2009 373; 1275-81.

Krum, H. et. al. Pharmacologic Management of the Cardiorenal Syndrome in Heart FAilure. Current Heart Failure Reports 2009, 6: 105-111.

Kudo et al., "Study on Mechanism of Cell Damage Caused by Microbubbles Exposed to Ultrasound." Ultrasound in Medicine & Biology, vol. 29, Supplement: 4pp, 2003.

Lalonde et al., "Field conjugate acoustic lenses for ultrasound hyperthermia." Ultrasonics, Ferroelectrics and Frequency Control, IEEE Transactions, vol. 40, Issue 5: Abstract 1pg., Sep. 1993.

Martin et al., Hemostasis of Punctured Vessels Using Doppler-Guided High Intensity Ultrasound, Ultrasound in Med.& Biol., vol. 25, pp. 985-990, 1999, USA.

Meyers, D. "Multiresolution tiling." Computer Graphics, No. 5: 325-340, 1994.

Miller et al., "A Review of In Vitro Bioeffects of Inertial Ultrasonic Cavitation From a Mechanistic Perspective." Ultrasound in Medicine & Biology, vol. 22, No. 9: 1131-1154, 1996.

Miller et al., "Diagnostic ultrasound activation of contrast agent gas bodies induces capillary rupture in mice." PNAS, vol. 97, No. 18: 10179-10184, 2000.

Moss, Nicholas G. Renal Function and Renal Afferent and Efferent Nerve Activity. American Journal Physiology. 243 (Renal Fluid Electrolyte Physiology) 12: F425-F433, 1982.

n.a., "Breast Cancer—Insightec: focused ultrasound for non invasive treatment." FAQ, Oct. 14, 2004. (http://www.exablate2000.com/physicians_faq.html).

n.a., "Cavitation." Ultrasound TIP—U.S. Database: Dec. 12, 2007.

n.a., "Mechanical Bioeffects in the Presence of Gas-Carrier Ultrasound Contrast Agents." Journal of Ultrasound & Medicine, vol. 19: 120-142, 2000.

Ng et al., "Therapeutic Ultrasound: Its Application in Drug Delivery." Medicinal Research Reviews, vol. 22, No. 2: 204-233, 2002.

Notice of Allowance dated Mar. 25, 2003 from U.S. Appl. No. 09/696,076, filed Oct. 25, 2000.

Office Action dated Apr. 29, 2011 for U.S. Appl. No. 12/202,195.

Office Action dated Apr. 6, 2010 for U.S. Appl. No. 11/619,996.

Office Action dated Aug. 17, 2006 from U.S. Appl. No. 10/671,417, filed Sep. 24, 2003.

Office Action dated Feb. 18, 2011 for U.S. Appl. No. 11/583,656.

Office Action dated Jan. 7, 2011 for U.S. Appl. No. 12/762,938.

Office Action dated Jul. 14, 2009 for U.S. Appl. No. 11/619,996.

Office Action dated Jul. 31, 2007 from U.S. Appl. No. 10/671,417, filed Sep. 24, 2003.

Office Action dated Jul. 5, 2006 for U.S. Appl. No. 10/616,831.

Office Action dated Jul. 9, 2008 for U.S. Appl. No. 11/486,528.

Office Action dated Jun. 28, 2010 for U.S. Appl. No. 12/247,969.

Office Action dated Mar. 18, 2011 for U.S. Appl. No. 12/247,969.

Office Action dated Mar. 4, 2011 for U.S. Appl. No. 11/583,569.

Office Action dated Nov. 16, 2010 for U.S. Appl. No. 12/202,195.

Office Action dated Nov. 29, 2002 from U.S. Appl. No. 09/696,076, filed Oct. 25, 2000.

Office Action dated Oct. 19, 2009 for U.S. Appl. No. 11/486,526.

Office Action dated Oct. 19, 2009 for U.S. Appl. No. 11/583,256.

Office Action dated Sep. 16, 2010 for U.S. Appl. No. 11/583,656.

O'Leary et al., "Carotid-artery Intima and Media Thickness as a Risk Factor for Myocardial Infarction and Stroke in Older Adults." Cardiovascular Health Study Collaborative Research Group. New England Journal of Medicine, vol. 340, No. 1: 14-22, Jan. 7, 1999.

Ostensen et al., "Characterization and Use of Ultrasound Contrast Agents." Academy of Radiology, vol. 9, Suppl. 2: S276-S278, 2002.

Owaki et al., "The Ultrasonic Coagulating and Cutting System Injuries Nerve Function." Endoscopy, vol. 34, No. 7: 575-579, 2002.

Pernot, et al., "Temperature Estimation Using Ultrasonic Spatial Compound Imaging", IEEE Transactions on Ultrasonics, Ferroelectrics, and Frequency Control, (May 2004) 51(5):606-615.

Pignoli et al., "Intimal plus medial thickness of the arterial wall: a direct measurement with ultrasound imaging." Circulation, vol. 74, No. 6:1399-1406, Dec. 1986.

Poliachik et al., "Activation, Aggregation and Adhesion of Platelets Exposed to High-Intensity Focused Ultrasound." Ultrasound in Medicine & Biology, vol. 27, No. 11: 1567-1576, 2001.

Poliachik et al., "Effect of High-Intensity Focused Ultrasound on Whole Blood With or Without Microbubble Contrast Agent." Ultrasound in Medicine & Biology, vol. 25, No. 6: 991-998, 1999.

Porter et al., "Ultrasound, Microbubbles and Thrombolysis." Progress in Cardiovascular Diseases, vol. 44, No. 2: 101-110, Oct. 2001.

Recchia et al., Ultrasonic Tissue Characterization of Blood during Stasis and Thrombosis with a Real-Time Linear-Array Backscatter Imaging System., Coronary Artery Disease, 1993, 4:987-994.

Rivens et al., "Vascular Occlusion Using Focused Ultrasound Surgery for Use in Fetal Medicine." European Journal of Ultrasound, vol. 9: 89-97, 1999.

Rose, Joseph, "Source Influence" Ultrasonic Waves in Solid Media, pp. 200-227, Cambridge University Press, 1999, USA.

Rosen et al., "Vascular Occlusive Diseases." 37pp., revised 2002.

Rosenschein et al., "Shock-Wave Thrombus Ablation, A New Method for Noninvasive Mechanical Thrombolysis." The American Journal of Cardiology, vol. 70, Issue 15: Abstract, Nov. 15, 1992.

Rosenschein et al., "Ultrasound Imaging-Guided Noninvasive Ultrasound Thrombolysis-Preclinical Results." Circulation, vol. 102: 238-245, 2000. (http://www.circulationaha.com.org).

Sanghvi et al. "High-Intensity Focused Ultrasounds." Experimental and Investigational Endoscopy. 4(2):383-395 (1994).

Schlaich, MP. Sympathetic Activation in Chronic Renal Failure. Journal American Society Nephrology 20: 933-939, 2009.

Schulte-Altedorneburg et al., "Accuracy of In Vivo Carotid B-Mode Ultrasound Compared with Pathological Analysis: Intima-Media Thickening, Lumen Diameter, and Cross-Sectional Area." Stroke, vol. 32, No. 7: 1520-1524, 2001.

Sheahan et al., Observing the Bracial Artery through a Pressure Cuff, Physiol. Meas. 14 (1993) 1-6.

Sherrit et al., The Characterisation and Modelling of Electrostrictive Ceramics for Transducers, Ferroelectrics, 228:(1-4), pp. 167-196, 1999.

Shrout et al., Classification of Electrostrictive-Based Materials for Transducers, 1993.

Shung, et al., "Ultrasonic Characterization of Blood During Coagulation", J. Clin. Ultrasound, (1984) 12:147-153.

Simon, et al, "Two-Dimensional Temperature Estimation Using Diagnostic Ultrasound", IEEE Transactions on Ultrasonics, Ferroelectrics, and Frequency Control, (Jul. 1998) 45(4):1088-1099.

Tachibana et al., "Albumin Microbubble Echo-Contrast Material as an Enhancer for Ultrasound Accelerated Thrombolysis." Circulation, vol. 92: 1148-1150, 1995.

Tachibana et al., "The Use of Ultrasound for Drug Delivery." Echocardiography, vol. 18, No. 4: 323-328, May 2001.

Tardy et al., "In Vivo Ultrasound Imaging of Thrombi Using a Target-specific Contrast Agent." Academy of Radiology, vol. 9, Suppl. 2: S294-S296, 2002.

ter Haar. G. Ultrasound Focal Beam Surgery. Ultrasound in Medicine and Biology. 21(9):1089-1100 (1995).

Vaezy et al., "Hemostasis of Punctured Blood Vessels Using High Intensity Focused Ultrasound," Ultrasound in Med.& Biol., vol. 24, No. 6, pp. 903-910,1998, USA.

Vaezy et al., "Acoustic surgery." Physics World: 35-39, Aug. 2001.

Vaezy et al., "Hemostasis and Tumor Treatment using High Intensity Focused Ultrasound: Experimental Investigations and Device Development." First International Workshop on the Application of HIFU in Medicine: 46-49, 2001.

Vaezy et al., "Hemostasis using high intensity focused ultrasound." European Journal of Ultrasound, vol. 9: 79-87, 1999.

Vaezy et al., "Intra-operative acoustic hemostasis of liver: production of a homogenate for effective treatment." Ultrasonics, vol. 43: 265-269, 2005.

Vaezy et al., Use of High-Intensity Focused Ultrasound to Control Bleeding, Mar. 1999, J Vasc Surg, vol. 29, pp. 533-542.

Valente, JF et. al. Laparoscopic Renal Denervation for Intractable ADPKD Related Pain. Nephrology Dialysis and Transplantation. 2001 16:160.

Von Land et al., "Development of an Improved Centerline Wall Motion Model." IEEE: 687-690, 1991.

Watkin et al., "Multi-Modal Contrast Agents: A First Step." Academy of Radiology, vol. 9, Suppl. 2: S285-S287, 2002.

Wickline et al., "Blood Contrast Enhancement with a Novel, Non-Gaseous Nanoparticle Contrast Agent." Academy of Radiology, vol. 9, Suppl. 2: S290-S293, 2002.

Williamson et al., "Color Doppler Ultrasound Imaging of the Eye and Orbit." Survey of Ophthamology, vol. 40, No. 4: 255-267, 1996.

Yu et al., "A microbubble agent improves the therapeutic efficiency of high intensity focused ultrasound: a rabbit kidney study." Urological Research, PubMed: Abstract, 2004.

* cited by examiner

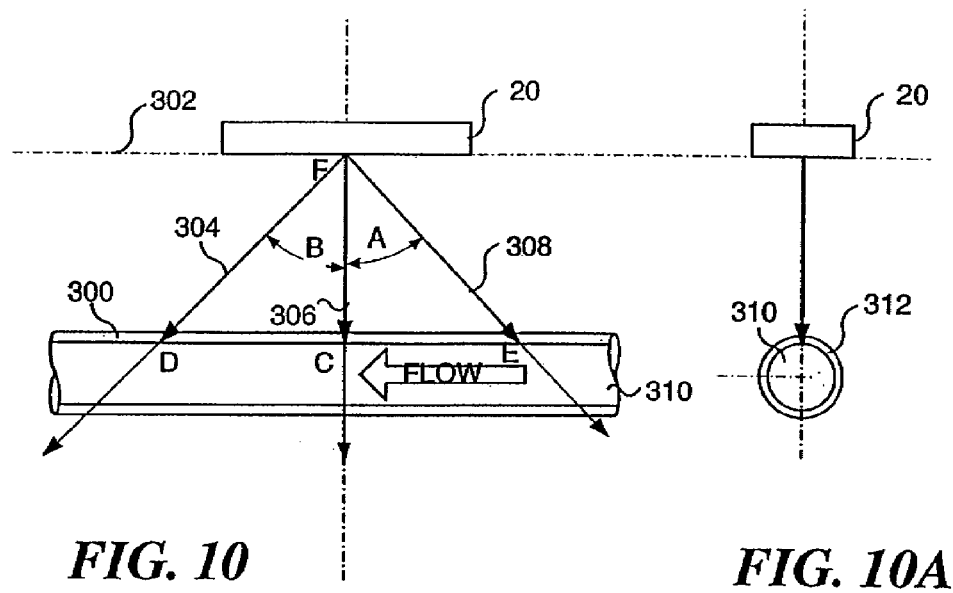
FIG. 10   FIG. 10A
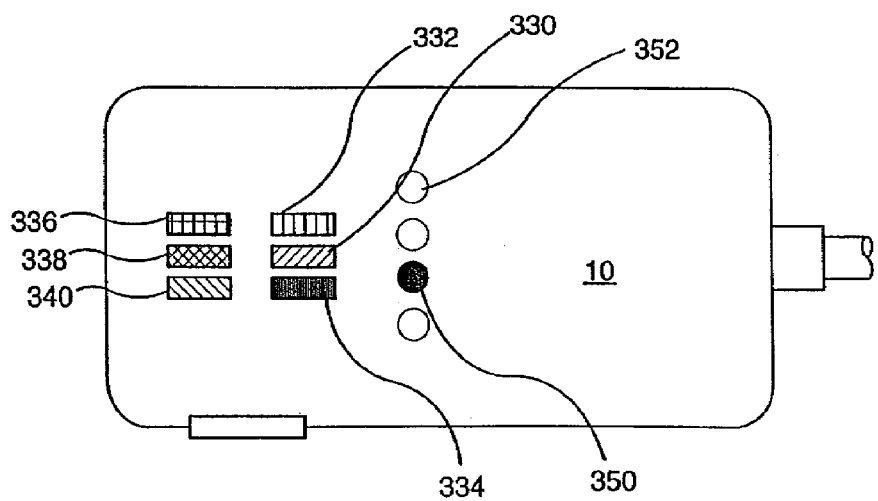
FIG. 11

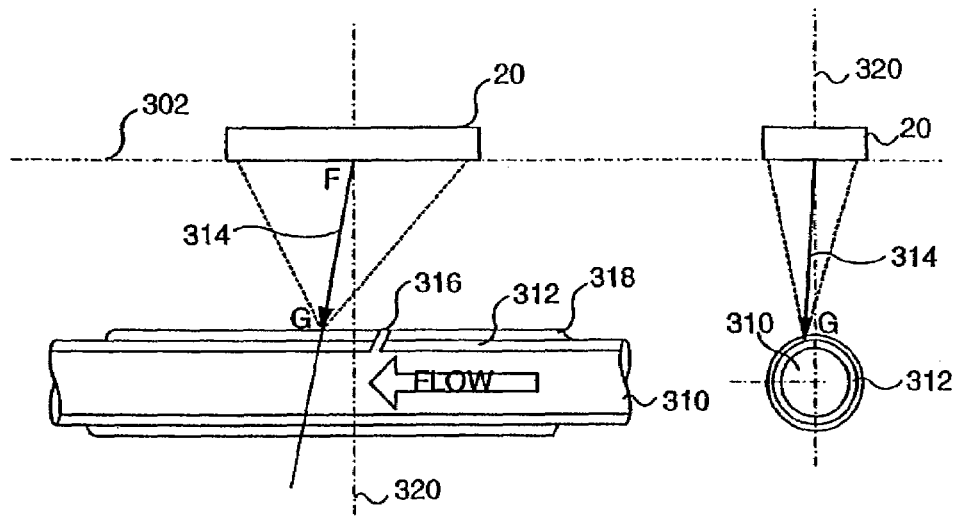
*FIG. 12A*    *FIG. 12B*
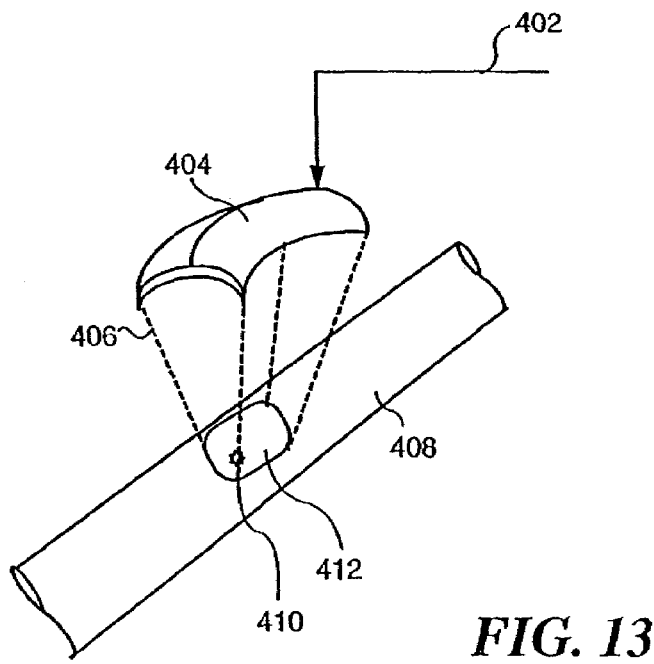
*FIG. 13*

METHODS TO DELIVER HIGH INTENSITY FOCUSED ULTRASOUND TO TARGET REGIONS PROXIMATE BLOOD VESSELS

RELATED APPLICATIONS

This application is a continuation of co-pending U.S. application Ser. No. 12/896,740, filed Oct. 1, 2010, which is a continuation of U.S. application Ser. No. 11/619,996, filed Jan. 4, 2007, which is a continuation of co-pending U.S. application Ser. No. 10/616,831, filed Jul. 10, 2003, which is a continuation of U.S. application Ser. No. 09/696,076, filed Oct. 25, 2000, now U.S. Pat. No. 6,656,136, which claims the benefit of U.S. provisional patent application Ser. No. 60/163,466, filed Oct. 25, 1999, and U.S. provisional patent application Ser. No. 60/171,703, filed Dec. 23, 1999.

FIELD OF THE INVENTION

The present invention generally relates to methods and apparatus for sealing vascular punctures and wounds, and more particularly, to a device that may be used to deliver ultrasound energy to a vascular puncture site to arrest bleeding.

BACKGROUND OF THE INVENTION

Various surgical procedures are performed by medical specialists such as cardiologists and radiologists, utilizing percutaneous entry into a blood vessel. To facilitate cardiovascular procedures, a small gauge needle is introduced through the skin and into a target blood vessel, often the femoral artery. The needle forms a puncture through the blood vessel wall at the distal end of a tract that extends through the overlying tissue. A guide wire is then introduced through the bore of the needle, and the needle is withdrawn over the guide wire. An introducer sheath is next advanced over the guide wire; the sheath and guide wire are left in place to provide access during subsequent procedure(s). The sheath facilitates passage of a variety of diagnostic and therapeutic instruments and devices into the vessel and its tributaries. Illustrative diagnostic procedures include angiography, intravascular ultrasonic imaging, and the like; exemplary interventional procedures include angioplasty, atherectomy, stent and graft placement, embolization, and the like. After this procedure is completed, the catheters, guide wire, and introducer sheath are removed, and it is necessary to close the vascular puncture to provide hemostasis and allow healing.

The most common technique for achieving hemostasis is to apply hard pressure on the patient's skin in the region of the tissue tract and vascular puncture to form a blood clot. Initially, pressure is applied manually and subsequently is maintained through the use of mechanical clamps and other pressure-applying devices. While effective in most cases, the application of external pressure to the patient's skin presents a number of disadvantages. When applied manually, the procedure is time-consuming and requires the presence of a medical professional for thirty minutes or more. For both manual and mechanical pressure application, the procedure is uncomfortable for the patient and frequently requires the administration of analgesics to be tolerable. Moreover, the application of excessive pressure can occlude the underlying artery, resulting in ischemia and/or thrombosis. Even after hemostasis has apparently been achieved, the patient must remain immobile and under observation for hours to prevent dislodgment of the clot and to assure that bleeding from the puncture wound does not resume. Renewed bleeding through the tissue tract is not uncommon and can result in hematoma, pseudoaneurisms, and arteriovenous fistulas. Such complications may require blood transfusion, surgical intervention, or other corrective procedures. The risk of these complications increases with the use of larger sheath sizes, which are frequently necessary in interventional procedures, and when the patient is anticoagulated with heparin or other drugs.

In recent years, several hemostasis techniques have been proposed to address the problem of sealing vessel wall punctures following percutaneous transcatheter procedures. Related prior art is described in U.S. Pat. Nos. 5,320,639; 5,370,660; 5,437,631; 5,591,205; 5,830,130; 5,868,778; 5,948,425; 6,017,359; and 6,090,130. In each of these patents, bioabsorbable, thrombogenic plugs comprising collagen and other materials are placed proximal to the vessel wall puncture site to stop bleeding. The large hemostasis plug stimulates blood coagulation in the vessel puncture site, but blocks the catheter entry tract, making catheter reentry more difficult, if required.

Other related prior art disclosed in U.S. Pat. Nos. 5,707,393; 5,810,884; 5,649,959; and 5,350,399 provides for the use of small dissolvable disks or anchors that are placed in the vessel to block or clamp the puncture hole. However, any device remaining in the vessel lumen increases the risk of thrombus formation. Such a device also can detach and cause occlusion in a distal blood vessel, which would likely require major surgery to remove.

Additional prior art includes U.S. Pat. Nos. 5,779,719; 5,496,332; 5,810,850; and 5,868,762. In the disclosure of these patents, needles and sutures delivered through catheters are used to ligate the puncture. The suturing procedure requires particular skill. Suture material left in the vessel may cause tissue irritation that will prolong the healing process.

Still other prior art is disclosed in U.S. Pat. No. 5,626,601, wherein a procoagulant is injected into the puncture, with a balloon catheter blocking inside the vessel lumen. However, in some cases, the clotting agent may leak past the balloon into the vessel lumen and cause stenosis.

Yet other prior art references related to this topic include U.S. Pat. Nos. 4,929,246; 5,810,810; and 5,415,657, which disclose the use of a laser or of radio-frequency (RF) energy that is transmitted to the blood vessel through a catheter to thermally fuse or weld the punctured tissue together.

All of the above cited prior art references require either introducing and leaving foreign objects in the patient's body, and/or inserting a tubular probe of large diameter into the tissue channel left by the catheter in order to seal the puncture.

As will be evident from the preceding discussion, there is a clear need for an improved method and apparatus for sealing a puncture left in a blood vessel, following an intravascular catheterization procedure. The method and apparatus should cause rapid cessation of bleeding, not rely on blood clot formation, and should be independent of the patient's coagulation status. By employing such a method and apparatus, the patient will be more comfortable as a result of shortened hemostasis and ambulation times, and physician and hospital resources will thereby be minimized. In addition, the method and apparatus should not leave any foreign object in the patient's body, to reduce the risk of stenosis at or distal to the puncture wound. An ideal device will be noninvasive and should not include any component that must be inserted in the catheter tract and which might further damage the wound and impede the sealing process.

SUMMARY OF THE INVENTION

In accord with the present invention, a method and apparatus are defined that provide advantageous solutions to the problem of expeditiously and safely sealing vascular catheter entry wounds made in connection with medical procedures. The method includes the steps of determining a site of the puncture in the vascular vessel and positioning an ultrasonic transducer applicator at a position adjacent to the site. The ultrasonic transducer applicator is coupled to a control that includes a processor programmed to administer ultrasonic energy in a manner that efficaciously seals a puncture. A user is enabled to initiate a process that is controlled by the control, so that very little operator training is required. The control automatically controls the ultrasonic transducer applicator so that the ultrasonic energy produced by the ultrasonic transducer applicator is focused at the site and is administered at a sufficient intensity and duration to denature tissue at the puncture, closing and sealing the puncture.

To determine the site of the puncture, an imaging ultrasonic beam is generated with the ultrasonic transducer applicator and is transmitted into the patient, proximate an expected location for the site. A reflection of the imaging ultrasonic beam is then received from within the patient using the ultrasonic transducer applicator, producing a corresponding output signal. The output signal is processed with the processor included in the control to facilitate determining the site of the puncture.

For example, a visual indication of a location of the site of the puncture can be provided to enable an operator to position the ultrasonic transducer applicator so that the ultrasonic energy produced by the ultrasonic transducer applicator is directed at the site. Such a visual indication may be in the form of, for example, lighted display indicators. In one form of the present invention, the visual indication includes an image of the site in which an axis of the vascular vessel is visually evident, enabling the operator to position the ultrasonic transducer applicator longitudinally along the axis of the vascular vessel so that the ultrasonic energy is directed at the site of the puncture.

In an alternative embodiment, an object is provided that extends into the puncture from outside the patient. The operator can then estimate the location of the puncture along the longitudinal axis of the vessel based upon a disposition of the object extending outside the patient. As yet a further alternative, the visual indication includes an image of the site in which the object extending into the puncture is evident. An estimate is made of the location of the puncture based upon a disposition of the object in the image.

Finally, the output signal can be processed with the processor to determine the site of the puncture. An indicator disposed on the ultrasonic transducer applicator can be controlled by the processor to provide an indication of a direction in which the ultrasonic transducer applicator should be moved to position it adjacent to the site of the puncture.

The processor is preferably used for automatically controlling at least one of a direction, an intensity, and a focus of the ultrasonic energy, to ensure that the ultrasonic energy is administered to the site of the puncture. Using the processor, the ultrasonic energy is directed so as to overscan the site of the puncture, ensuring that the puncture is closed and sealed. For example, the processor can move the focus of the ultrasonic energy while it is being administered, to overscan the site of the puncture. As another alternative, an ultrasound emitter of the ultrasonic transducer applicator has an aspheric shape so that the ultrasonic energy that is directed at the site of the puncture covers a larger area that overscans the site. Other transducer configurations that provide a laterally broadened focal region may also be employed.

Preferably, the ultrasonic transducer applicator uses a common array of transducers for generating both the imaging ultrasound beam and the ultrasound energy that closes and seals the puncture.

It is also contemplated that the administration of the ultrasonic energy be interrupted, to again generate the imaging ultrasound beam, thereby confirming whether the ultrasonic energy is being directed at the site of the puncture.

The processor is preferably employed to control a force applied against a surface of the patient using a force generator included in the ultrasonic transducer applicator. This force is controlled so that a pressure developed by the force is sufficient to substantially stop fluid leakage from the vascular vessel, but not so great as to substantially occlude fluid flow through the vascular vessel.

Another aspect of the invention is directed to enclosing the unit applicator within a protective, acoustic coupling shell. The protective, acoustic coupling shell is adapted to contact an external dermal portion of the patient in order to convey the ultrasonic energy transdermally to the site of the puncture, while isolating an ultrasonic emitter surface on the ultrasonic transducer from direct, contacting exposure to the patient. The protective, acoustic coupling shell is preferably pre-sterilized and preferably includes a gel patch on an outer surface that is protected by a tab. The tab is removed prior to contacting the external dermal surface of the patient.

Still another aspect of the present invention is directed to apparatus. The apparatus include elements that carry out functions generally consistent with the steps of the method discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 2:
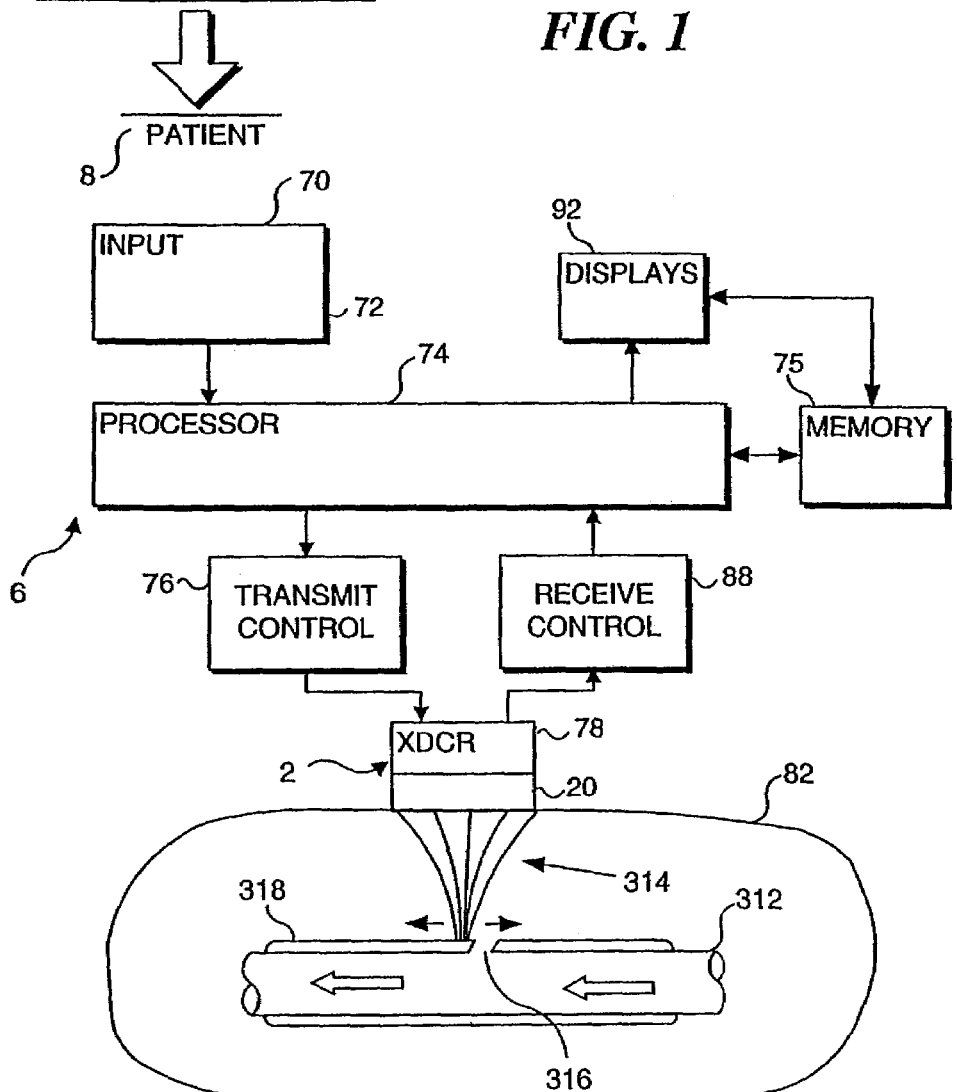
FIG. 2 is a schematic diagram illustrating how the present invention is employed for sealing a puncture in a vessel.
Figure 3:
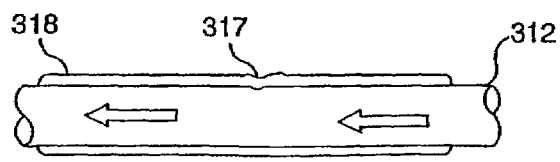
Figure 4:
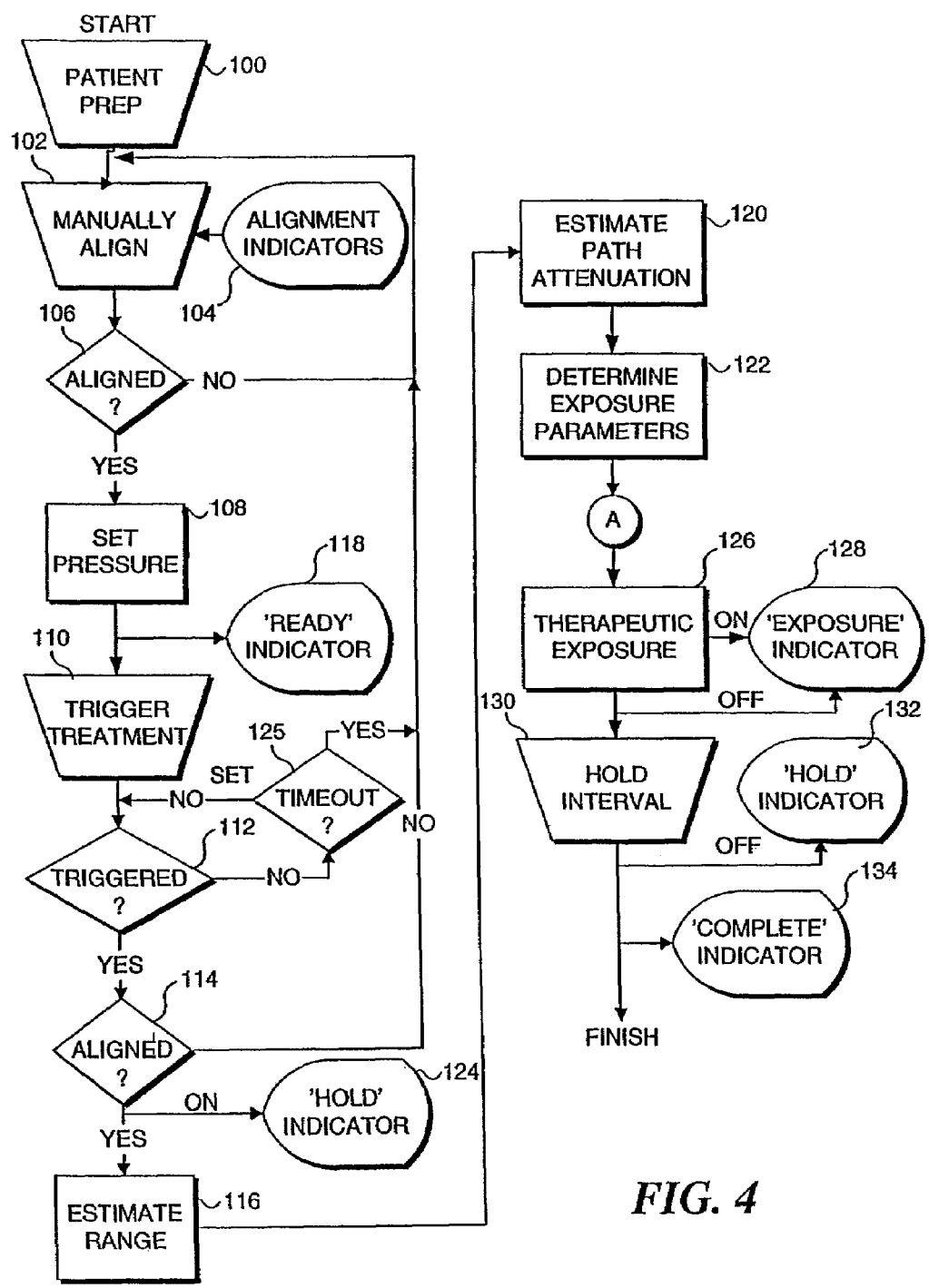
Figure 4A:
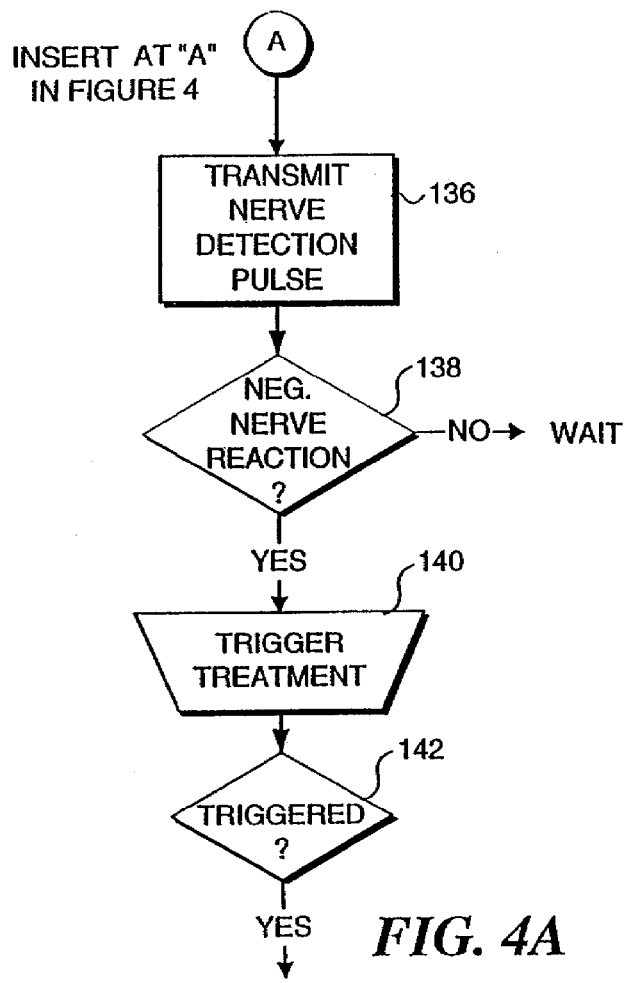
Figure 5:
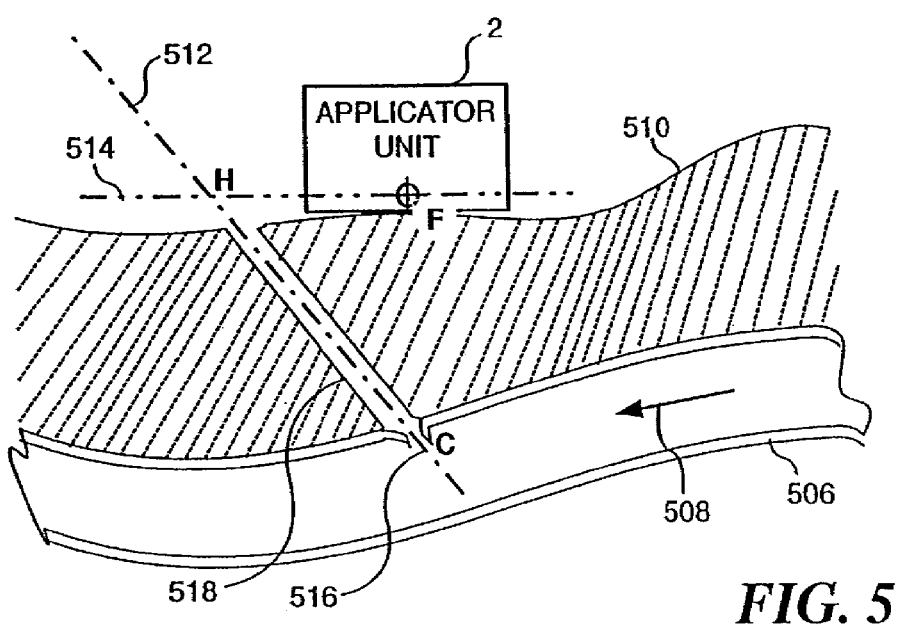
Figure 6:
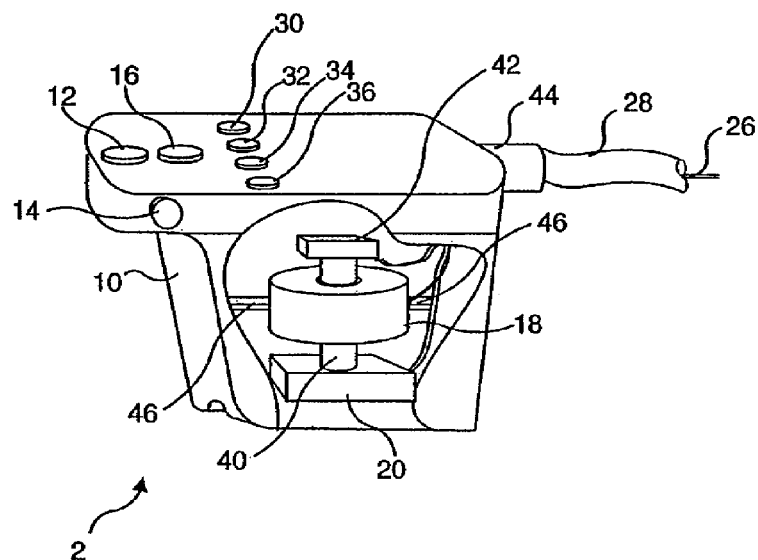
Figure 6A:
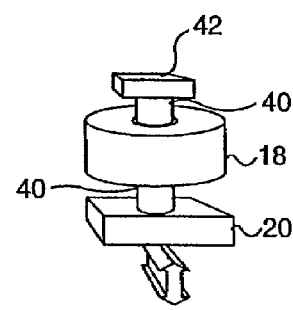
Figure 7:
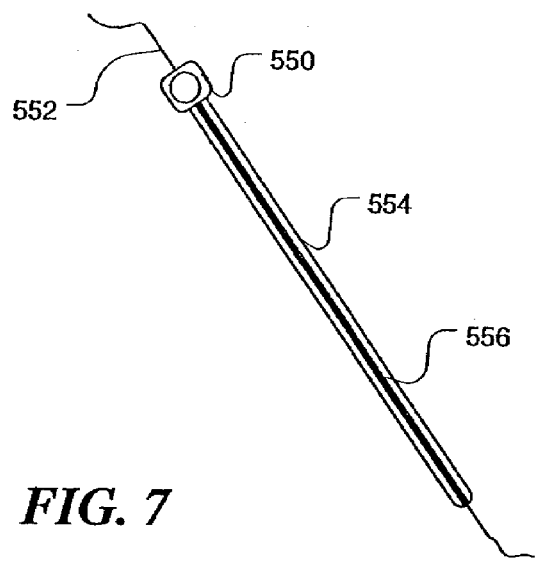
Figure 7A:
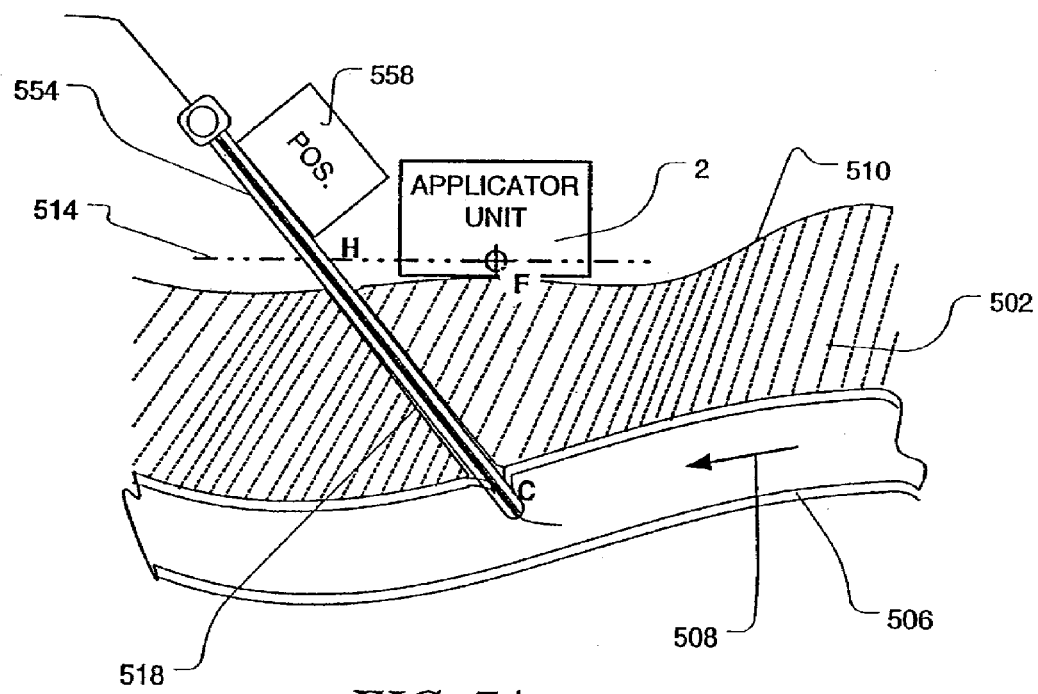
Figure 7B:
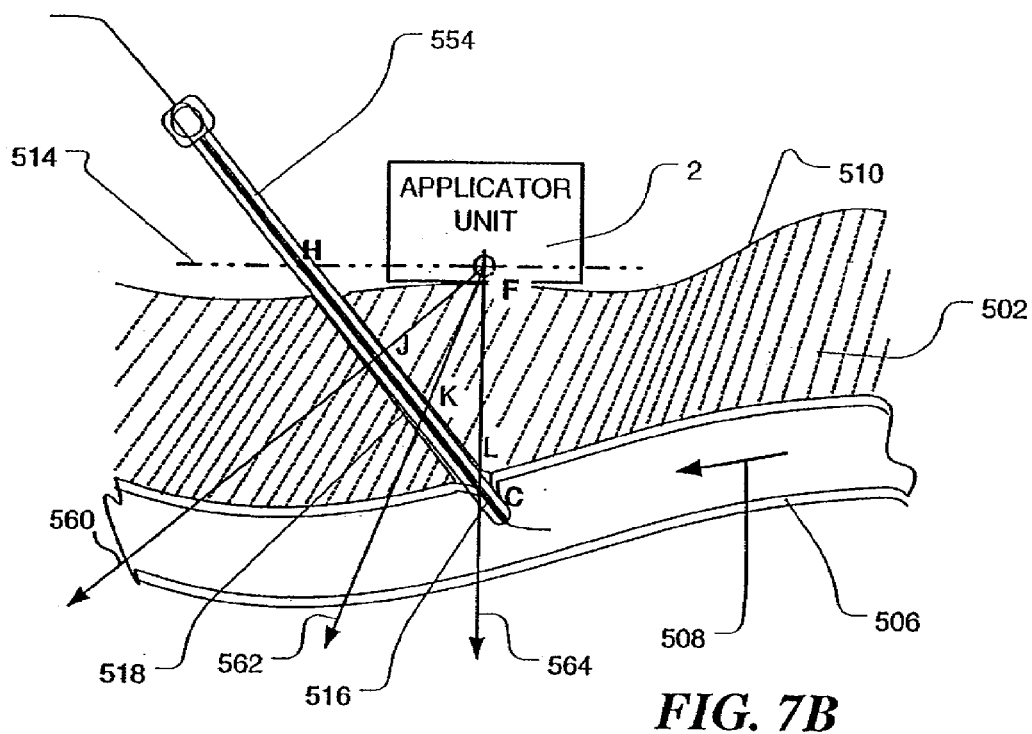
Figure 7C:
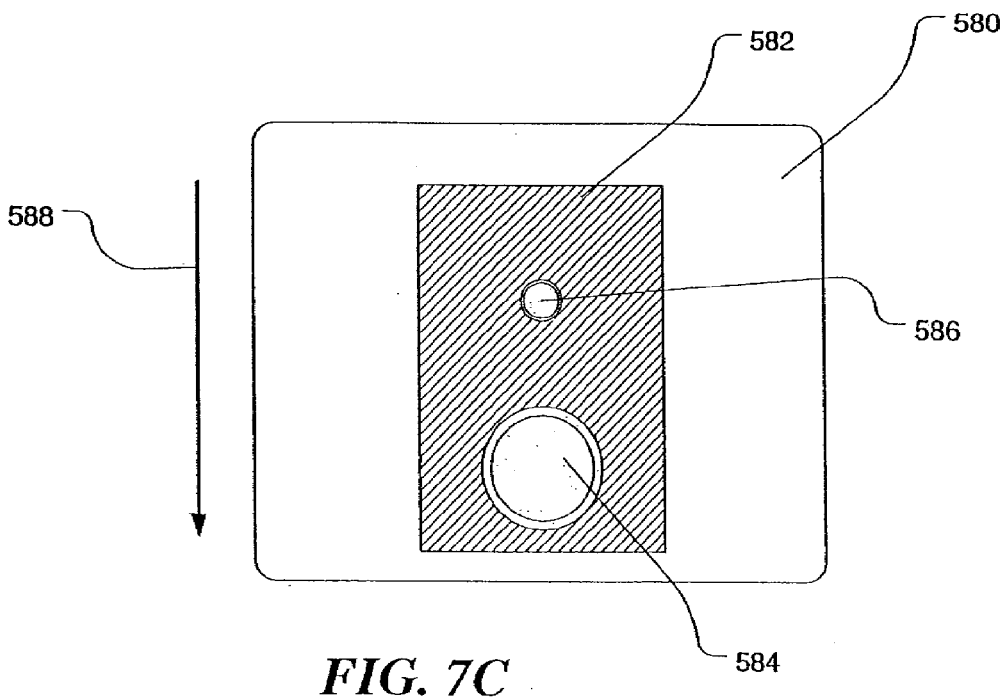
Figure 8:
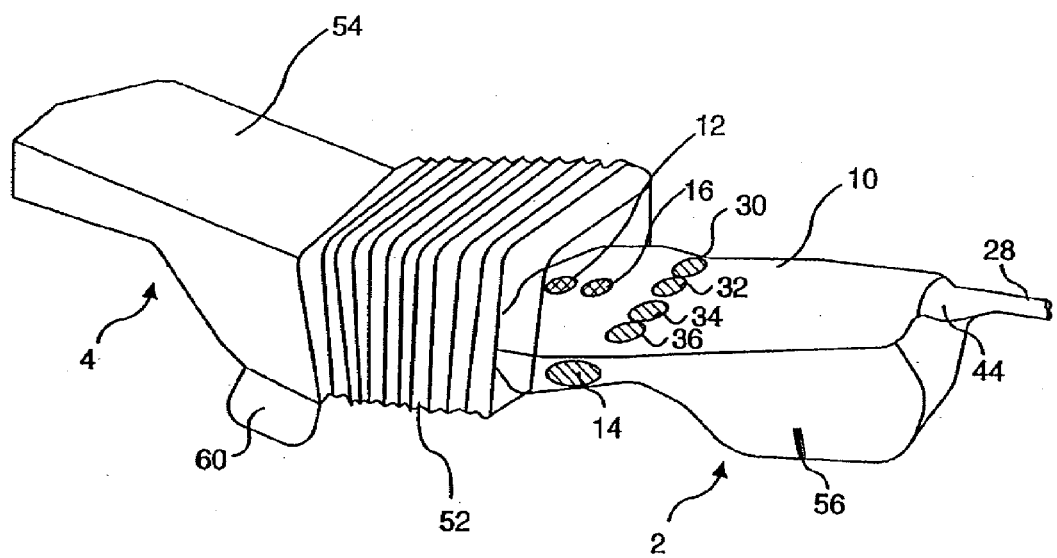
Figure 8A:
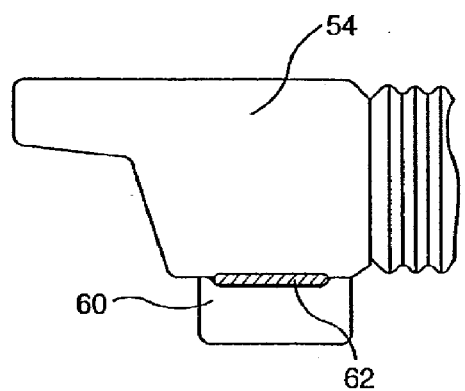
Figure 9:
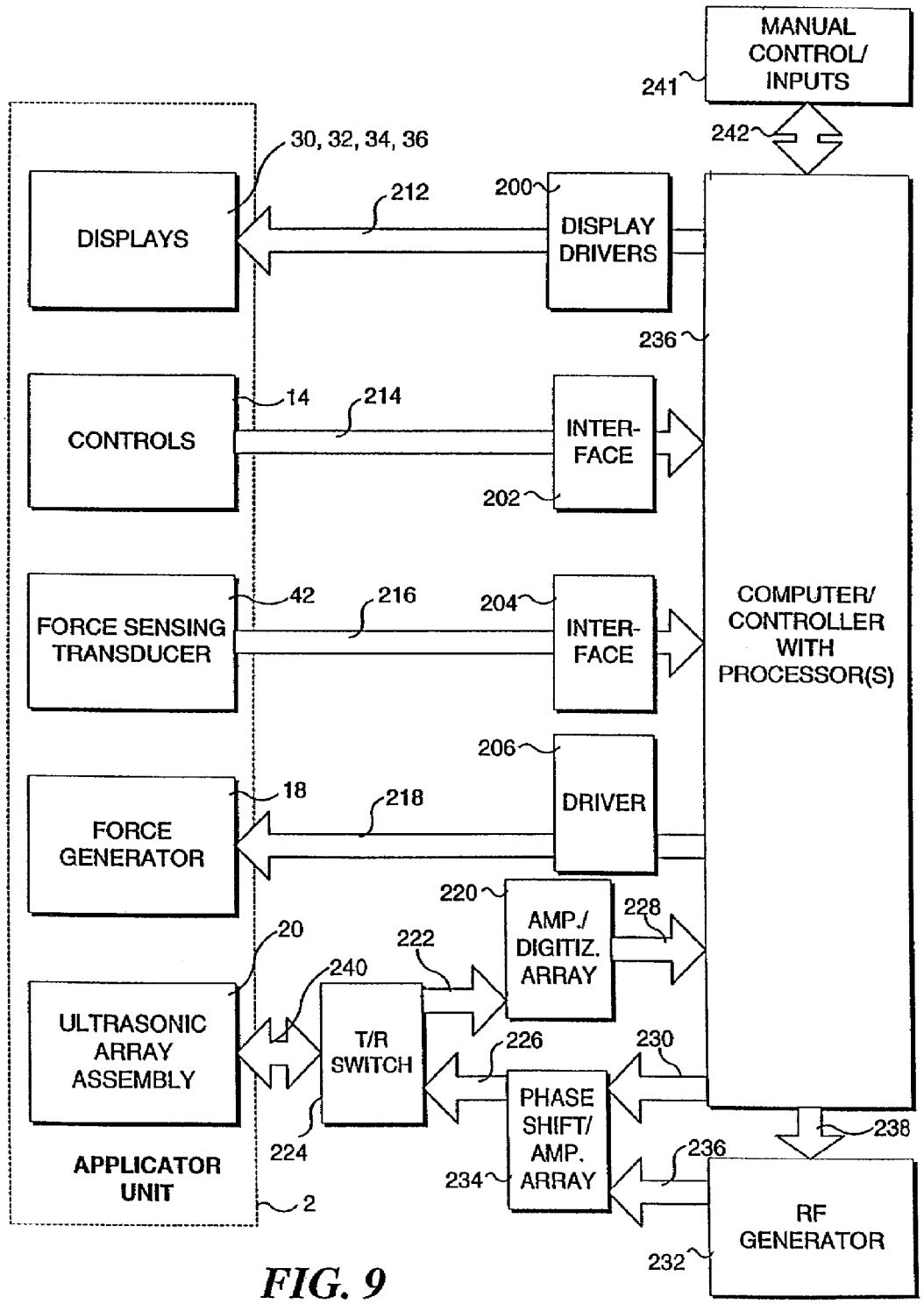

FIG. 3 schematically illustrates a collagen seal produced by the present invention to close the puncture in the vessel of FIG. 2;

FIG. 4 is a flow chart illustrating the logical steps followed during sealing of a vascular wound in accord with the present invention;

FIG. 4A is a flow chart illustrating the optional steps employed for detecting nerves during the method of FIG. 4;

FIG. 5 is a cross-sectional view of a portion of a patient's body, illustrating an applicator unit in accord with the present invention disposed adjacent to a puncture that extends transdermally into an artery;

FIG. 6 is a cutaway isometric view of the applicator shown in FIG. 5;

FIG. 6A is an isometric view showing the force sensing transducer, force generator, and ultrasonic array of the applicator;

FIG. 7 is an elevational view of a locator rod adapted to be inserted into a puncture wound over a guide wire;

FIG. 7A is a cross-sectional view of a portion of a patient's body like that in FIG. 5, illustrating the locator rod of FIG. 7 being used to determine a location of a puncture in the artery relative to the applicator unit;

FIG. 7B is similar to FIG. 7A, but illustrates the use of ultrasonic pulse-echo techniques to determine the spatial location of the locator rod;

FIG. 7C depicts a view of a framed two-dimensional image a target region generally orthogonal to that shown in FIG. 7A and FIG. 7B, for use in locating the puncture site;

FIG. 8 is a schematic isometric view of an embodiment of the applicator that uses a disposable shell;

FIG. 8A is an side view of the disposable shell of FIG. 8;

FIG. 9 is a schematic system block diagram depicting modules included in the applicator and control unit;

FIGS. 10 and 10A respectively illustrate the ultrasound beam orientation relative to the vessel from the side of the vessel and as viewed along the vessel;

FIG. 11 is a plan view of an embodiment of the applicator illustrating the controls and indicators that it includes;

FIGS. 12A and 12B respectively illustrate the side and longitudinal geometry of the therapeutic ultrasound beam; and FIG. 13 is an isometric view illustrating the ultrasound beam geometry produced by an aspheric transducer.

DESCRIPTION OF THE PREFERRED EMBODIMENT

Use of Ultrasound for Sealing Punctures

Because of its unique properties in soft tissue, ultrasound can be brought to a tight focus at a distance from its source. If sufficient energy is radiated within the ultrasound beam, cells located in the focal volume can be rapidly heated, while intervening and surrounding tissues are spared. Surrounding tissues are unaffected in the unfocused portion of the ultrasound beam because the energy is spread over a correspondingly larger area and associated heating is minimized.

Whereas ultrasound intensities on the order of 0.1 Watts/$cm^2$ are employed in diagnostic imaging applications, intensities in excess of 1,000 Watts/$cm^2$ are typical in high-intensity focused ultrasound (HIFU) applications. At the focal point, these high intensities result in large, controlled temperature rises within a matter of seconds.

It has been demonstrated in numerous in vivo animal studies that HIFU can rapidly seal blood vessel punctures and lacerations over a wide range of sizes. When accurately targeted on a vascular wound, ultrasound has been shown to induce complete hemostasis in less than one minute in the femoral, carotid, and axillary arteries, and in the femoral and jugular veins of large animals, while blood flow through the treated vessels remained unaffected. These investigations included: (a) sealing punctured, surgically exposed vessels using visual targeting, (b) sealing incised, surgically exposed vessels using visual targeting, (c) sealing surgically exposed, punctured vessels using Doppler-guided ultrasound targeting, and (d) noninvasive sealing of punctured vessels under ultrasound imaging guidance wherein complete hemostasis was noted in 13±12 seconds.

The mechanism of hemostasis in these ultrasound-exposed vascular wounds appears thermal in origin and involves denaturization of native perivascular collagen with subsequent formation of an extensive fibrin network that covers the hole, thereby sealing it closed. The fibrin links with adjacent vessel wall tissues to form a seal that has been shown to be independent of puncture hole size. Acoustic streaming forces generated by the HIFU beam were also observed to play a role in opposing the escape of blood from the vascular wound. Blood clotting is not believed to be a factor in achieving acoustic hemostasis, as evidenced by equally rapid and complete wound sealing in highly anticoagulated animals and in ex vivo vessels in which saline has been substituted for blood.

Overview of the Present Invention

Figure 1:
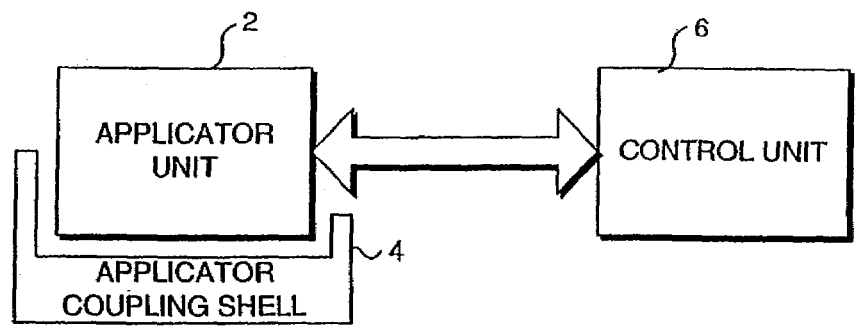
FIG. 1 is a schematic block diagram of the primary components employed in a preferred embodiment of the present invention.

FIGS. 1 and 2 show the main components of an ultrasonic system suitable for use in implementing the present invention. As illustrated in FIG. 1, a hand-held applicator unit 2 is positioned over an arterial wound 8 in the patient. Included with the hand-held applicator unit is a generally single-use, pre-sterilized cover and acoustic coupling shell 4 that slips over applicator 2. A control unit 6 implements algorithms to facilitate the method and is coupled to applicator 2.

The user enters various conventional scan and control parameters into an input unit 70, which typically includes user input devices 72. Examples of such devices include a keyboard, knobs, and buttons. The input unit is connected to a processing system 74, which will typically comprise a plurality of microprocessors and/or digital signal processors. Processing system 74 may, however, also be implemented using a single processor of sufficient speed to handle the various tasks described below. A conventional memory 75 will normally be included in the system to store, among other data, transmission control parameters and imaging data generated in any given implementation of the present invention.

Processing system 74 sets, adjusts, and monitors the operating parameters of a conventional transmission and control circuit 76. Control circuit 76 forms a transmit ultrasonic waveform by generating and applying electrical control and driving signals to an ultrasound transducer 78, which preferably comprises an array of individually controllable piezoelectric elements. As is well known in the art, the piezoelectric elements generate ultrasonic waves when electric, signals of a proper frequency are applied to them; conversely, when receiving reflected ultrasonic waves, they generate electrical signals corresponding to the mechanical vibrations caused by the returning ultrasonic waves.

Transducer 78 is positioned against it portion 82 of the body of a patient, and by varying the phasing, amplitude, and timing of the driving signals for the transducer array elements, ultrasonic waves are focused to form a transmit beam 314 of high-intensity ultrasound.

In FIG. 2, open arrows indicate the direction of a flow of blood within a blood vessel 312, which has a puncture site 316 that may have been caused by introduction of a catheter or, in the case of unintended punctures that have produced wounds, by some other object. The tissue forming a layer 318 of collagen found on the surface of blood vessels is also shown in FIG. 2 surrounding blood vessel 312.

As will be clear from the description of the present invention below, it is not necessary for the system to include an imaging capability. However, the provision of an imaging capability, including pulse-echo lines of interrogation that are not displayed as images, in the present invention should assist a user to more accurately locate a vascular puncture site. It is recognized that a full display of the insonified vascular target site is not required.

Nonetheless, since imaging of a vascular target site is preferable and will employ echo processing (especially, Doppler), FIG. 2 also illustrates a reception controller 88, which will include conventional amplification and signal conditioning circuitry as needed. Reception controller 88, all or part of which is normally integrated into processing system 74, converts the ultrasonic echo signals (which are typically at radio frequencies, on the order of a few to tens of megahertz) into lower frequency ranges for processing and may also include analog-to-digital conversion circuitry. The processing includes, as needed, such known signal conditioning as time-gating, gain compensation, Doppler frequency shift processing, and diffraction compensation, in order to identify echo signals from any selected focal region. The type of conventional signal processing needed (if any) will in general depend on the particular implementation of the present invention employed and can be implemented using known design methods.

Note that it is not essential, according to the present invention, that the transducer 78 be used externally, relative to the patient's body. It is also contemplated that the transducer may be maneuvered inside a patient's body, and the beam focused on a puncture from inside the body. For example, a transesophageal probe, laparoscopic, or other probe inserted into a body cavity, such as the vagina or rectum can be used to practice the present invention. A suitably designed probe inserted into an open body cavity or via minimally invasive means could be used to arrest bleeding in surgical or trauma care situations. Yet, most of the following discussion is directed to a preferred embodiment of the present invention in which the transducer is intended to be used externally, since an initial commercial product in accord with the present invention will be designed for such use.

A conventional display system 92 may also be included in order to display information concerning transmission power, time, focus data, etc. The display system will include known circuitry for scan conversion and for driving the display, as needed. These circuits are well known and therefore need not be specifically illustrated or described further to provide an enabling disclosure.

FIG. 3 illustrates the result of an insonification of puncture site 316 using the present invention. As the focal point of transmit beam 314 (see FIG. 2) is moved around (as illustrated by the arrows pointing in either direction from the focus of the beam) the area of puncture site 316 using conventional beam-steering techniques, the tissue adjacent the puncture site 316 will denature. In effect, the collagen in the tissue "melts" and flows over and into the puncture opening. When the collagen cools, it forms a "patch" that not only covers the puncture, but also flows partially into the puncture opening in the wall of the blood vessel. Moreover, since the denatured tissue tends to contract, it also tends to pull the edges of the puncture together and thus further close the wound.

It should be noted that the present invention can be employed to seal vascular wounds of various types and is not limited to the type of wound created as a result of interventional procedures in which a catheter has been introduced into a vascular vessel. As noted above, application of thermal treatment to the tissue overlying a wound has been demonstrated to seal the wound. In the present invention, a practical method has been developed for repeatedly and reliably achieving sealing of the puncture in a vascular vessel. Steps carried out in this method are shown in FIG. 4, which is discussed below. These steps represent one preferred embodiment of the present invention, but do not represent all alternatives that might be employed to achieve acceptable sealing.

Key steps in the method for vascular sealing described here include:
1. Positioning an ultrasound generating source on a patient such that the source is targeted at an area including the wound to be sealed;
2. Applying a pressure against the patient in an area overlying the wound and directed substantially toward the vessel to be treated;
3. While the pressure and the positioning of the ultrasound source are maintained, carrying out an insonification of a volume of tissue that includes the wound, using an ultrasound exposure that delivers an acoustic energy density (measured at the approximate location of the wound), in excess of 100 joules/sq. cm, but generally less than several thousand joules/sq. cm.

Additional steps of the method described below employ the apparatus in an automated manner that facilitates ease of use and ensures the safety and consistency of the results obtained.

A clinically acceptable device for sealing a puncture wound in accord with the present invention must meet a number of requirements, including:
1. The device and associated procedure must be safe to use in that they avoid undesirable bioeffects, so that the patient is not injured directly or indirectly as a result of the procedure; also, in the event that effective vessel sealing does not occur as desired, traditional methods of applying pressure to the wound are sufficient to accomplish hemostasis;
2. The device and associated procedure must be easy to use in an efficient manner, to facilitate proper, repeatable execution of the sealing process; requirements for operator training should be minimized;
3. The sealing process must be sufficiently fast to enable the entire procedure to be rapidly completed—preferably, in less than 5 minutes;
4. The cost per sealing procedure should be minimized; and,
5. The efficacy of the device should be very high, generally achieving a success rate in excess of about 95%; acceptability of the present invention in routine clinical practice does not permit an unpredictable outcome.

These requirements are met by the present invention, as described below, and as defined in the claims that follow. A preferred embodiment of the device includes the components shown in FIGS. 1 and 2, which were described above.

FIG. 6 and FIG. 6A show one preferred embodiment of applicator unit 2. The applicator unit includes an outer housing 10 having an ergonomically considered shape so that it can be conveniently hand held. The outer housing is best fabricated from an injection moldable plastic material such as ABS or the like. The operator grasps the outer housing of the applicator unit so as to enable a control push-button 14 to be accessible and indicators 12, 16 and 30, 32, 34, and 36 to be visible to the operator. Positioning the applicator unit at the appropriate location over the wound area and activation of an essentially automated treatment cycle are readily accomplished. The operator simply refers to the indicators to determine when the applicator unit is properly positioned and ready for use. Indicators 12 and 16 are used to indicate when alignment of the applicator unit with the longitudinal axis of the vessel to be sealed has been achieved. Indicators 30, 32, 34, and 36 display the state of operation and instruct the operator with respect to holding the applicator in place as described in detail later in this description. Control 14 when pressed, activates the treatment cycle, thus initiating a sequence of operations that determine ultrasonic scan parameters (exposure time, scan pattern, intensity, focal range, etc.).

As shown in FIG. 6A, ultrasonic array assembly 20 is held within outer housing 10 on a shaft 40, in a bearing assembly within a force transducer 18, so as to permit movement of the ultrasonic array assembly to and away from patient 8. Shaft 40 passes through the bearing assembly provided within a force generator 18 and terminates at a contacting force sensing transducer 42. Force generator 18 comprises an electromagnetic solenoid that is rigidly supported and mounted within housing 10 by structural members 46. The face of ultrasonic array assembly 20 is in contact with the appropriate location on the body of the patient (overlying the site of the puncture) and is thus capable of applying a substantially compressive, controllable force on the tissue structures with which it is in contact. The force applied by the ultrasonic array assembly is produced at least in part by controllably energizing force generator 18. Ultrasonic array assembly 20 preferably operates in a multiplicity of modes; however, separate ultrasonic transducers can instead be provided for some or all of the functions performed in a different design within the scope of the present invention.

In the illustrated preferred embodiment, electrical connections comprising wires 26 are routed within the outer housing 10 and out in a sealed bushing 44 that mounts a cable 28 to the control unit 6. Cable 28 is sufficiently long, on the order of 10 feet in length, so that the control unit may be conveniently located at a distance from the patient and operator location.

Applicator unit housing 10 is shaped to be used with a slip-on, generally single-use protective applicator shell 4 (illustrated schematically in FIG. 1). The shell employed in the preferred embodiment is shown in greater detail in FIGS. 8 and 8A. Shell 4 has side walls 54 that are fabricated from a generally optically transparent, semi-rigid plastic material. A skirt 52 extends from the rear of the shell and is pleated so that in preparing for use of the applicator unit, an operator can grasp the skirt and extend it sufficiently to protect a sterile area of the patient from coming into contact with cord. The protective shell is packaged in a sterile condition. The shell is fabricated from a flexible plastic material having low acoustic absorption characteristics. A fiducial mark 56 is provided on a side of the applicator unit and visible through the optically transparent material of the protective shell. This fiducial mark is employed to visually align the applicator unit with a position on the patient at which the applicator unit will be used to seal a puncture.

Sterile, generally gas free acoustic coupling gel 62 is deposited in a patch on the bottom of flexible bottom 58. Prior to use, the gel is held in place and sealed by semi-sticky adhesive coated tab 60. Tab 60 is removed by the operator just prior to use, thereby exposing the gel so that it provides a good acoustic coupling with the surface of the patient's body. Protective applicator shell 4 thus provides a sterile barrier over the multi-use applicator unit and conveniently provides a pre-determined amount of a specific appropriate acoustic coupling medium. Although not shown, it is contemplated that the bottom of the interior cavity of the shell may also include a layer of acoustic coupling gel to ensure good acoustic coupling between the applicator unit through the protective, applicator coupling shell.

With reference to FIG. 1, applicator unit 2 is connected to control unit 6. Power supplies, signal processing components, and control and RF power generation components are housed within control unit 6. FIG. 9 is a system block diagram illustrating the modules disposed, in the preferred embodiment, within the applicator unit 2 (i.e., the component shown within the dotted line portion of this Figure) as well as the modules (all other modules that are not in the applicator unit) disposed in the control unit 6. In this preferred embodiment, control unit 6 is packaged in a small, self-contained pole- or cart-mounted enclosure that derives its input power from a standard AC line power service (not shown). Power supplies with the unit are designed to assure low leakage currents for patient safe operation.

In the preferred embodiment the architecture of control unit 6 is based on a programmable processing unit which processes various signals and controls a number of functional modules. A microprocessor is well suited to perform the computation and control functions required. Applicator unit 2 is coupled to control unit 6 by a plurality of signal paths 212, 214, 216, and 218. Signal path 212 couples display drivers 200, which are controlled by a computer/controller 236, with indicators 30, 32, 34, and 36 on the applicator unit. Control button 14 on the applicator unit is coupled through signal line 214 to an interface 202 and thus to the computer/controller. Force sensing transducer 42 produces an output signal indicative of the force (i.e., the pressure) applied against the surface of the patient's tissues by the applicator unit, and this signal is conveyed by signal lines 216 to an interface 204, which provides the signal to the computer/controller. In response to the magnitude of the monitored force, the computer/controller produces a control signal applied to a driver 206, which provides the current signal used to energize force transducer 16, to determine any additional force that it generates to achieve a desired pressure on the site of the puncture that is sufficient to prevent loss of fluid from the vessel, but not so great as to occlude the flow of fluid through the vessel.

Signal lines 240 couple ultrasonic array assembly 20 to a transmit/receive switch 224. The transmit/receive switch determines the operational mode of the ultrasonic array assembly under the control of the computer/controller. When operating in a diagnostic mode in which the ultrasonic array assembly is producing an imaging ultrasound beam, the signal corresponding to the echo reflected received by ultrasonic array assembly 20 from tissue and other structures is conveyed through transmit/receive switch 224 and through signal lines 222 to an amplifier digitizer array 220. The output signals from the amplifier digitizer array are conveyed to computer/controller 236 through signal lines 228. When the ultrasonic array assembly is generating either the imaging beam or the HIFU beam, it is responding to signals received from an RF generator 232 that is coupled to a phase shift/amplifier array 234 by signal lines 236, and to a control signal provided by the computer/controller and conveyed to the phase shift/amplifier on a signal line 230. The output of the phase shift/amplifier is conveyed on signal lines 226 to transmit/receive switch 224, and thus, to ultrasonic array assembly 20 through signal lines 240. Manual control inputs 241 are coupled to computer/controller 236 through signal lines 242.

A number of variously advantageous transducer configurations may alternatively be employed in this invention. Possibilities include:

Configurations wherein therapeutic and, pulse-echo Doppler functionality are accomplished by the same ultrasonic transducer or by separate ultrasonic transducers; and, Configurations wherein the ultrasonic transducer is either of a fixed focus type, or a segmented electrically selectable macro element array, or a phased array, or a linear array, or an annular array; and, Configurations where a large focal spot 412 (see FIG. 13) (e.g. a focal spot produced by a transducer having an aspheric shape), or those in which a tightly focused spot is produced; and, Configurations wherein the ultrasonic transducer is mechanically positioned (or scanned), or those in which it is fixed in one position.

An aspheric ultrasonic transducer configuration has the advantage of covering a large treatment area on the surface of the vessel without the complication of electronic or mechanical beam steering. Covering a large area (i.e., overscanning) is desired in order to ensure that the actual site of the puncture wound is treated, given its positional ambiguity. FIG. 13 depicts the geometry of such a configuration. In this embodiment, an ultrasonic transducer 404, excited by an appropriate RF source via connections 402, is generally aspheric in shape and does not bring the ultrasound beam to a sharp focus. The ultrasonic energy that it produces covers area 412 on a vessel 408 that includes puncture wound 410. Fluid or solid material acoustic coupling (not shown) is used between the ultrasonic transducer and the tissues of the patient.

In one preferred embodiment, the method described includes a series of manual steps (operator actions) and automated steps. The automated steps are carried out as control processes or algorithms executed by one or more processors and other hardware in accord with machine instructions executed by the one or more processors. It is understood that variations in the order of these steps, and in the total complement of steps implemented is possible in alternative embodiments. Steps as shown in FIG. 4 are described as follows.

In a step 100 labeled Patient Preparation, the operator positions the patient and the apparatus so that the applicator unit is conveniently positioned over the puncture wound area, e.g., over the puncture made by a catheter in the femoral artery. Shell 4 is removed from its sterile package and fitted onto applicator unit 2, and gel sealing tab 60 (shown in FIGS. 8 and 8A) is removed, exposing the gel 62.

A step 102 labeled Manually Align is then carried out. With the catheter introducer in the wound, the operator palpates the area locating the point at which the introducer just enters the artery. The operator marks this location on the patient's skin with a suitable marking device (e.g. a surgical marker), drawing a line substantially perpendicular to the perceived direction of the artery, extending approximately 3 cm from the entry wound location. It is the purpose of this marking to estimate the longitudinal location of the wound; the operation of the HIFU sealing process provides for an overscan of the wound area so that practical variations in the operator's ability to make the longitudinal position estimate are permissible. Other techniques for locating the site of the puncture are discussed below. In a more preferred embodiment, lateral and range locations of the wound are more precisely located by the automated capability of the processor(s) used in the apparatus.

Also within step 102, the operator places the device over the wound location, aligning fiducial mark "56" (shown in FIG. 8) with the line that was drawn on the patient's skin. The applicator unit is rotated in place until both alignment indicators 12 and 16 (FIGS. 6 and 8) illuminate, indicating that the artery is axially aligned under the applicator unit.

The axial alignment indications are, in this preferred embodiment, derived from two ultrasonic pulsed Doppler interrogations. FIGS. 10 and 10A show the geometry of the Doppler alignment beams. Use of a ultrasonic transducer 20 enables the same ultrasonic transducer to be employed to produce an imaging beam and the HIFU beam for both a pulse-echo targeting mode and a therapeutic mode.

In the alignment sequence illustrated in FIGS. 10 and 10A, phased array ultrasonic transducer 20 sends and receives a downstream pulsed Doppler line 304 and an upstream line 308 sequentially. Lines 304 and 308 are in plane with the axial centerline of the applicator unit and a line perpendicular to the bottom surface of the applicator unit. Lines 304 and 308 are transmitted at angles A and B with respect to a line 306, which is perpendicular to the applicator unit. Angles A and B are chosen to provide a axial separation as well as an appreciable vector flow component in the direction of the interrogating line—an angle of approximately 45 degrees. Direction of flow in an interior 310 of the vessel is sensed and tested to assure that an artery 300 (not a vein) is being interrogated. Doppler signals, from lines 304 and 308, integrated over an appropriate range, above a pre-determined threshold value, are used to cause the illumination of alignment indicators 12 and 16 respectively. Averaging multiple lines is, in this preferred embodiment, employed to improve the performance of the alignment detection scheme. The conditioned signals also set logical flags so that the system may interlock the initiation of a therapeutic treatment sequence with assurance of alignment. Thus in a decision step 106 (FIG. 4), alignment is tested by interrogating the logical presence of both of the flags.

Alternatively, another advantageous configuration for guiding the manual alignment process uses multiple Doppler lines and multiple indicators, with reference to FIG. 11, which illustrates a top view of the applicator unit. In this configuration, three parallel lines are transmitted and received in the two directions indicated by lines 304 and 308 in FIG. 10. Additional transducers are appropriately positioned in housing 10 (FIG. 6). Pulsed Doppler signals are processed in a manner similar to that described above. Thus, for example (referring to FIG. 11), if the alignment is off-center and rotated to the left, indicator lights 336 and 334 would be illuminated, indicating the misalignment and suggesting the appropriate direction to move the applicator unit to achieve alignment (denoted when indicators 338 and 330 are illuminated). Alternatively, continuous wave Doppler may be employed to interrogate the flow position of the target artery, with operation essentially similar to that described above.

With verified alignment in step 106. the system proceeds to a step 108 labeled Set Pressure, wherein the pressure over the artery is set and controlled within a predetermined range using force generator 18 (FIG. 6) and force sensing transducer 42. In this preferred embodiment, the weight of the applicator unit is purposefully made to be in a range where additional pressure applied by the operator to hold the unit firmly in place is reduced. This useful weight is about 1 lb (0.45 kg) or more. Force generator 18 is activated and controlled such that applied pressure to the artery partially restricts flow, but maintains sufficient flow so that thermal cooling due to blood flow within the artery protects the intimal lining of the vessel from irreversible damage. Presence of a Doppler flow signal on down-stream line 304 (FIG. 10) is employed to assure vessel patency.

In this preferred embodiment, when the system has completed the pressure application cycle described above, indicator 32 (FIG. 6), which is marked "READY" on the applicator unit is illuminated (see block 118 FIG. 4), indicating to the operator that a treatment cycle may be manually initiated (triggered) by pushing control button 14. The system is in a wait state as indicated in a decision block 112 in FIG. 4, until a manually triggered treatment cycle is detected. With the detection of a triggered treatment cycle, axial alignment is verified in a step 114 by generally repeating the logical test described at step 102.

A step 116 then makes a ranging measurement to estimate the acoustic path length between ultrasonic transducer assembly 20 and the vessel boundary. i.e. the distance between points F and C along line 306 in FIG. 10. Pulsed Doppler is, in this preferred embodiment, employed to make this measurement, wherein lines 304 and 308 measure distances F-D and F-E, respectively. Points D and E are recognized by the fact that these correspond to the first instance of flow detected along each line as range increases. The range estimate of FC is therefore:

$$FC \sim (FE \cos A + FD \cos B)/2 \quad \text{Equation 1}$$

A step 120 estimates the acoustic attenuation at the therapeutic frequency between ultrasonic transducer assembly 20 and the target collagen layer overlaying the vascular wound, path F-C in FIG. 10. In this preferred embodiment, a simplified approach is employed wherein estimated dimension FC is used to access data in a look-up table of attenuation values. Attenuation values in the table are predetermined by empirical measurement. Alternatively, more sophisticated A-Mode attenuation measurements may be employed to assess to F-C path.

A step 122 determines the therapeutic ultrasound exposure parameters to be employed. Dimension F-C, the attenuation estimate, and optionally, patient parameters (e.g., size and weight), input at module 240 in FIG. 9, are used to access predetermined data and scan protocols in resident look-up tables Ultrasound scan geometry, intensity and epochal exposure intervals are thus determined.

Ultrasound scan geometry, intensity and time parameters are determined to accomplish three key objectives: (1) provide a sufficient overscan of a longitudinal and lateral surface of the target vessel so as to include the site of the wound; (2) ensure delivery of an appropriate energy dose to the collagen layer in the region of the target site to raise its temperature to a range of between 60 and 100 degrees Celsius for a predetermined period of time; and, (3) assure that the skin and interpath tissue is not exposed to a temperature-time exposure that will result in pain and or irreversible tissue damage.

Therapeutic scan geometry is shown in FIGS. 12A and 12B. A therapeutic level of approximately 50 watts total transmitted acoustic power, generally weakly focused, is transmitted along a centerline 314 through a dermal layer 302. The desired scan pattern is achieved by directing the beam over varying angles of the beam with respect to a line 320 that extends perpendicular to the center of the face of the application unit. Thus, for example, a raster scan pattern may cover a therapeutic area, over collagen layer 318, of dimensions 1 cm wide by 1.5 cm long (in the arterial axial direction). Such an overscan of the wound site provides for variations in the operator's ability to predetermine and locate the precise lateral position of the wound, as well as the variation in wound location that results from the possible variation of wound lateral entry points. Importantly, scan geometry is selected such that ultrasonic exposure is generally confined to the vessel, minimizing the possibility that an adjacent vein or nerve structure will be insonified.

A step 126 carries out the therapeutic exposure cycle. It is generally desirable to hold the applicator unit in place, providing the established orientation and pressure for a period of time after the therapeutic exposure cycle. A hold interval 130 (FIG. 4) is selected to enable exposed tissue structures to cool, a time period of approximately 1 minute. Following this time period, indicator 36 on the application unit (FIG. 6) marked "COMPLETE" is illuminated and the "HOLD" indicator is turned off, instructing the operator that the therapeutic treatment is completed and the device may be removed from the patient.

In situations where there is concern for inadvertent exposure of a nerve structure, an additional sequence depicted in FIG. 4A may optionally be employed. The sequence is inserted into the process flow of FIG. 4, in this preferred embodiment, at a location marked "A." To detect the presence of a nerve structure, a weak, sub-therapeutic energy level ultrasonic pulse is transmitted in a step 136 (FIG. 4A), to cover the determined target area. The operator observes in a decision step 138 whether a reaction of pain and or uncommanded movement from the patient has occurred, indicating that a nerve structure has been stimulated. System logic then waits for an addition manually initiated trigger input in steps 140 and 142, prior to proceeding with therapeutic exposure at step 126 in FIG. 4.

Alternative Techniques for Aligning the Applicator Unit

Step 102, which facilitates alignment of the applicator unit over the wound area and targeting of the therapeutic exposure, may be accomplished using several alternative approaches compared to that described above. It is desired to employ an approach for targeting and aligning the applicator unit that is easy to implement and requires minimum operator instruction. The approach further should be consistent with minimizing bleeding during the process of achieving alignment. Additionally, the approach should be robust and provide targeting of .the wound site with sufficient accuracy such that the wound will reliably be included within the area of therapeutic exposure.

A principle employed in the present invention is the concept that the overscan of the target location during therapeutic exposure is sufficient to accommodate targeting ambiguity and possible patient or operator movement during the procedure. Nevertheless, accurate targeting is needed to ensure efficacy of the wound sealing process.

In the preferred embodiment described above, pulsed Doppler ranging was employed to locate the axis of the vessel, and the operator was advised of the longitudinal location of the wound on the vessel by reference to visual landmarks on the skin surface. Alternatively, by inclusion of additional automation, the need for the operator to locate the longitudinal position is eliminated, thereby substantially simplifying the targeting procedure for the operator.

These alternative approaches make use of the entry channel along which the introducer and guide wire are commonly passed during diagnostic and interventional catheterization procedures. FIG. 5 illustrates the geometry that relates the location of applicator unit 2 to the locations of an entry channel 518 and a vessel wound 516. In FIG. 5, applicator unit 2 is positioned on a patient's skin surface 510 over a vessel 506 in which a blood flow 508 is contained. A location "C" is indicated at wound 516; a line 512 passes from "C" through entry channel 518, intersecting a plane 514 defined by reference locations on applicator unit 2 at a point "H." A point "F" is a reference point in plane 514. If the spatial location of line 512 is known relative to plane 514 and point "F," and the vector distances "H" to "F", or "C" to "F" are known, then the location of wound 516 relative to applicator unit 2 is determinable by basic geometry. Knowledge of this geometry permits automated system function to be employed to provide guidance instructions (e.g. visual indicators) to the operator during the manual alignment portion of the procedure.

A sufficient number of the parameters in the above described geometry may be determined by several novel methods and their associated apparatus. As previously described, acoustic pulsed Doppler may be employed to determine the distance "C"-"F" (reference FIG. 5). In many applications of the vascular sealing method described herein, the vessel is an artery having a substantial high velocity flow and is thus readily localized using well known pulsed Doppler techniques. Knowing this distance, localization of wound 516 on the vessel is made possible by determining the spatial position of line 512.

The spatial location of line 512 may be determined by employing a substantially rigid, straight locator rod 554 as depicted in FIG. 7, which is placed in entry channel 518. Locator rod may have a longitudinal center bore 556 through which a guide wire 552 may pass. In practical use, the introducer used in conjunction with a clinical procedure would be removed without removing the guide wire. Locator rod 554 would be introduced into the wound over the guide wire. Sealing assembly 550 is disposed at one end of the locator rod to prevent the loss of blood through center bore 556.

Several alternative approaches may be employed to determine the spatial location of the longitudinal axis of locator rod

554 and thus, to determine precise wound location as described above. These approaches include:

1. As shown in FIG. 7A, a spatial position resolving element 558 may be included on locator rod 554. Spatial position resolving element 558 may be an acoustic position sensor, an optical position sensor, a magnetic position sensor, an electromechanical positioning or resolving arm, or an inertial position sensor. The spatial relationship between the position of locator rod 554 and applicator unit 2 is accomplished by either a direct mechanical linkage or by way of an intermediate electronic or computational circuit.

2. As shown in FIG. 7B, an ultrasonic pulse-echo technique may be employed to determine the spatial location of locator rod 554. A transducer in applicator unit 2 transmits directed acoustic pulses in more than one direction, e.g., lines 560, 562, and 564, and echoes from structures in each path are returned and detected by a pulse-echo receiver included in the applicator unit, as is well know in the diagnostic ultrasound art. Locator rod 554 provides reflections that permit making time of flight measurements of, for example, distances "F"-"J," "F"-"K," and "F"-"L." Locator rod 554 may be coated or constructed of materials chosen to enhance acoustic reflectivity, thus providing echoes that are readily distinguished from background clutter. Common guide wires may alternatively be used as locator rod 554, as these wire structures are typically highly reflective of ultrasound energy. Alternatively, locator rod 554 may be constructed from materials that enhance reflection at a harmonic of the interrogating ultrasound pulse, providing another advantageous method for clearly distinguishing the echoes from locator rod 554 from those received from surrounding tissue. Materials or coatings that entrap gas bubbles are, for example, effective in providing higher harmonic reflection. Echo enhancing properties may also be incorporated into an introducer that is then used as the locator rod. Pulsed Doppler may also be employed to identify and locate the locator rod. In this latter alternative, the locator rod may be a common introducer. A strong Doppler shifted reflection will return from the lumen of the introducer even when blood is not permitted to flow out of the introducer.

3. As indicated in FIG. 7C, two dimensional, or three dimensional, imaging may also be employed to locate locator rod 554, the guide wire, and 'the introducer, as well as the vessel. FIG. 7C depicts a view of a framed two-dimensional image 580 of the target region generally orthogonal to that shown in FIGS. 7A and 7B. Distance from the ultrasound source increases toward the bottom of this depiction. This image is generally representative of a cross-sectional plane of interrogation located at a line 562 in FIG. 7B. Automated image recognition provided by the processor may be employed to identify structures including locator rod 554, imaged as a locator rod structure 586 and vessel 506, imaged as a vessel structure 584 in this image. Doppler imaging and color flow mapping may be employed to increase the recognizablility of relevant features. The interrogating image plane may be scanned over the region containing the target. When locator rod structure 586 is recognized at a location just touching the top surface of vessel structure 584. the wound target. site has been identified.

Although the present invention has been described in connection with the preferred form of practicing it, those of ordinary skill in the art will understand that many modifications can be made thereto within the scope of the claims that follow. Accordingly. it is not intended that the scope of the invention in any way be limited by the above description, but instead be determined entirely by reference to the claims that follow.

What is claimed is:

1. A method of non-invasively applying heat to a region proximate to a blood vessel target, the method comprising:
   generating an imaging ultrasonic beam adapted to image the blood vessel target, the blood vessel target having a puncture site;
   receiving a reflection of the imaging ultrasonic beam and in response producing a corresponding output signal;
   processing the output signal to identify a location of a treatment zone proximate an outer wall of the blood vessel target;
   detecting the presence of a nerve structure adjacent to the blood vessel target by applying an ultrasonic pulse to the treatment zone;
   applying a therapeutic ultrasound energy beam to the treatment zone, wherein the ultrasound energy beam is a high intensity focused ultrasound energy beam; and
   moving the therapeutic ultrasound energy beam to over-scan the treatment zone with therapeutic ultrasonic energy,
   wherein the imaging ultrasonic beam, the ultrasonic pulse, and the therapeutic ultrasound energy beam are transcutaneously applied.

2. The method of claim 1, wherein the therapeutic ultrasound energy beam is movable in a plurality of directions at any given time.

3. The method of claim 1, wherein the therapeutic ultrasound energy beam is applied by an ultrasonic transducer applicator.

4. The method of claim 3, wherein the ultrasonic transducer applicator comprises an array of transducers.

5. The method of claim 4, wherein the array of transducers is configured to emit the imaging ultrasonic beam.

6. The method of claim 1, further comprising the step of interrupting the application of the therapeutic ultrasound beam to generate a second imaging ultrasonic beam to confirm that the therapeutic ultrasound beam is being directed to the treatment zone.

7. The method of claim 1, wherein the intensity of the ultrasonic pulse is less than about 1,000 Watts per square centimeter.

8. A method of non-invasively applying heat to a region proximate to a blood vessel target, the method comprising:
   directing an imaging ultrasonic beam proximate the blood vessel target, the blood vessel target having a puncture site;
   receiving a reflection of the imaging ultrasonic beam;
   processing the reflection of the imaging ultrasonic beam to identify a location of a treatment zone proximate an outer wall of the blood vessel target;
   detecting the presence of a nerve structure adjacent to the blood vessel target by applying an ultrasonic pulse to the treatment zone;
   applying a high intensity focused ultrasound beam to the treatment zone; and
   moving the high intensity focused ultrasound beam to over-scan the treatment zone with therapeutic ultrasonic energy,
   wherein the imaging ultrasonic beam, the ultrasonic pulse, and the therapeutic ultrasound energy beam are transcutaneously applied.

9. The method of claim 8, wherein the high intensity focused ultrasound beam is movable in a plurality of directions at any given time.

10. The method of claim 8, wherein the high intensity focused ultrasound beam is applied by an ultrasonic transducer applicator.

11. The method of claim 10, wherein the ultrasonic transducer applicator comprises an array of transducers.

12. The method of claim 11, wherein the array of transducers is configured to emit the imaging ultrasonic beam.

13. The method of claim 8, further comprising the step of interrupting the application of the high intensity focused ultrasound beam to generate a second imaging ultrasonic beam to confirm that the high intensity focused ultrasound beam is being directed to the treatment zone.

14. The method of claim 8, wherein the intensity of the ultrasonic pulse is less than about 1,000 Watts per square centimeter.

15. The method of claim 1, wherein the presence of the nerve structure is determined based on the pain of a patient in response to the ultrasonic pulse.

16. The method of claim 1, wherein a direction of the therapeutic ultrasound energy beam is oriented with respect to a direction of flow in the blood vessel.

17. A method of applying heat to a region proximate to a blood vessel, the method comprising:
generating an imaging ultrasonic beam adapted to image a blood vessel target;
receiving a reflection of the imaging ultrasonic beam and in response producing a corresponding output signal;
processing the output signal to identify a location of a treatment zone proximate an outer wall of the blood vessel target;
detecting the presence of a nerve structure by applying an ultrasonic pulse to the treatment zone, the ultrasonic pulse having an intensity that is less than 1,000 Watts per square centimeter;
applying a therapeutic ultrasound energy beam to the treatment zone, wherein the ultrasound energy beam is a high intensity focused ultrasound energy beam; and
moving the therapeutic ultrasound energy beam to over-scan the treatment zone with therapeutic ultrasonic energy,
wherein the imaging ultrasonic beam, the ultrasonic pulse, and the therapeutic ultrasound energy beam are transcutaneously applied.

18. The method of claim 17, wherein the presence of the nerve structure is determined based on the pain of a patient in response to the ultrasonic pulse.

19. The method of claim 17, wherein a direction of the therapeutic ultrasound energy beam is oriented with respect to a direction of flow in the blood vessel.

20. The method of claim 17, wherein the therapeutic ultrasound energy beam is movable in a plurality of directions at any given time.

21. The method of claim 17, wherein the therapeutic ultrasound energy beam is applied by an ultrasonic transducer applicator.

22. The method of claim 21, wherein the ultrasonic transducer applicator comprises an array of transducers.

23. The method of claim 22, wherein the array of transducers is configured to emit the imaging ultrasonic beam.

24. The method of claim 17, further comprising the step of interrupting the application of the therapeutic ultrasound beam to generate a second imaging ultrasonic beam to confirm that the therapeutic ultrasound beam is being directed to the treatment zone.

25. A method of treating a patient, the method comprising:
directing an imaging ultrasonic beam proximate a blood vessel;
receiving a reflection of the imaging ultrasonic beam;
processing the reflection of the imaging ultrasonic beam to identify a location of a treatment zone proximate an outer wall of the blood vessel;
detecting the presence of a nerve structure by applying an ultrasonic pulse to the treatment zone, the ultrasonic pulse having an intensity that is less than 1,000 Watts per square centimeter;
applying a high intensity focused ultrasound beam to the treatment zone; and
moving the high intensity focused ultrasound beam to over-scan the treatment zone with therapeutic ultrasonic energy,
wherein the imaging ultrasonic beam, the ultrasonic pulse, and the therapeutic ultrasound energy beam are transcutaneously applied.

26. The method of claim 25, wherein the high intensity focused ultrasound beam is movable in a plurality of directions at any given time.

27. The method of claim 25, wherein the high intensity focused ultrasound beam is applied by an ultrasonic transducer applicator.

28. The method of claim 27, wherein the ultrasonic transducer applicator comprises an array of transducers.

29. The method of claim 28, wherein the array of transducers is configured to emit the imaging ultrasonic beam.

30. The method of claim 25, further comprising the step of interrupting the application of the high intensity focused ultrasound beam to generate a second imaging ultrasonic beam to confirm that the high intensity focused ultrasound beam is being directed to the treatment zone.

* * * * *